(12) United States Patent
Dumesic et al.

(10) Patent No.: US 8,148,553 B2
(45) Date of Patent: Apr. 3, 2012

(54) CATALYTIC CONVERSION OF CELLULOSE TO LIQUID HYDROCARBON FUELS BY PROGRESSIVE REMOVAL OF OXYGEN TO FACILITATE SEPARATION PROCESSES AND ACHIEVE HIGH SELECTIVITIES

(75) Inventors: James A. Dumesic, Verona, WI (US); Juan Carlos Serrano Ruiz, Madison, WI (US); Ryan M. West, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 309 days.

(21) Appl. No.: 12/490,129

(22) Filed: Jun. 23, 2009

(65) Prior Publication Data

US 2010/0324310 A1 Dec. 23, 2010

(51) Int. Cl.
*C07D 307/00* (2006.01)
*C07C 6/00* (2006.01)
*C07C 51/00* (2006.01)

(52) U.S. Cl. ......................... 549/326; 585/324; 562/515

(58) Field of Classification Search .................. 549/326; 585/324; 562/515
See application file for complete search history.

(56) References Cited

U.S. PATENT DOCUMENTS 3,065,263 A * 11/1962 Carlson ......................... 562/515
4,897,497 A 1/1990 Fitzpatrick
5,883,266 A 3/1999 Elliott et al.
2006/0162239 A1 7/2006 Van Den Brink et al.
2007/0208183 A1* 9/2007 Haan et al. ..................... 549/303

FOREIGN PATENT DOCUMENTS

EP 1 918 247 A1 5/2008
WO WO 89/10362 A1 11/1999
WO WO 2008/142127 A1 5/2008
WO WO 2007/099111 * 1/2009
WO WO 2009/007391 A1 1/2009

OTHER PUBLICATIONS

Heeres et al Green Chemistry (2009), 11(8), 1247-1255.*
Corma et al. Chemical Review, 2007, 107, 2411-2502.*
Hayashi et al. STN Accession No. 1955:60246;Document No. 49:60246, Abstract of Nippon Kagaku Kaishi (1921-47) (1954), Ind. Chem. Sect. 57, 67-9.*
Abbott et al., Kinetics of Reactions of $C_8$ Olefins on HY Zeolite, *J. Catal.*, (1987) 108, 346-355.
Chheda et al., Liquid-Phase Catalytic Processing of Biomass-Derived Oxygenated Hydrocarbons to Fuels and Chemicals, *Angew. Chem. Int. Ed.* (2007) 46(38), 7164-7183.
Christensen et al., The Renewable Chemicals Industry, *ChemSusChem*, (2008) 1, 283-289.
Cortright et al., Hydrogen from catalytic reforming of biomass-derived hydrocarbons in liquid water, *Nature* (2002) 418(6901) 964-967.

De Klerk, Oligomerization of 1-Hexene and 1-Octene over Solid Acid Catalysts, *Ind. Eng. Chem. Res.* (2005) 44, 3887-3893.
Gaertner et al., Catalytic coupling of carboxylic acids by ketonization as a processing step in biomass conversion, *Journal of Catalysis*, (2009) accepted.
Girisuta et al., Kinetic Study on the Acid-Catalyzed Hydrolysis of Cellulose to Levulinic Acid, *Ind. Eng. Chem. Res.* (2007) 46(6) 1696-1708.
Huber et al., Synergies between Bio- and Oil Refineries for the Production of Fuels from Biomass, *Angew. Chem. Int. Ed.* (2007), 46, 7184-7201.
Koppatz et al., $H_2$ rich product gas by steam gasification of biomass with in situ $CO_2$ absorption in a dual fluidized bed system of 8 MW fuel input, *Fuel Proc. Tech.* (2009) In Press.
Kumar et al., *Ind. Eng. Chem. Res.* (2009), 48, 3713-3729.
Kunkes et al., Catalytic Conversion of Biomass to MonofunctionalHydrocarbons and Targeted Liquid-Fuel Classes, *Science* (2008) 322 (5900) 417-421.
Mamman et al., Furfural: Hemicellulose/xylosepderived biochemical, *Biofuels Bioproducts & Biorefining* (2008), 2(5), 438-454.
Miller et al., A Highly Catalytic and Selective Conversion of Carboxylic Acids to 1-Alkenes of One Less Carbon Atom, *J. Org. Chem.* (1993) 58, 18-20.
Renz, Ketonization of Carboxylic Acids by Decarboxylation: Mechanism and Scope, *Eur J Org Chem* (2005) 979-988.
Robinson et al. The use of catalytic hydrogenation to intercept carbohydrates in a dilute acid hydrolysis of biomass to e ect a clean separation from lignin, *Biomass Bioenergy* (2004) 26(5), 473-483.
Serrano-Ruiz et al., Effect of the support composition on the vapor-phase hydrogenation of crotonaldehyde over $Pt/Ce_xZr_{1-x}O_2$ catalysts, *J. Catal.* 241 45 (2006).

(Continued)

*Primary Examiner* — Nizal Chandrakumar
(74) *Attorney, Agent, or Firm* — Joseph T. Leone, Esq.; DeWitt Ross & Stevens S.C.

(57) ABSTRACT

Described is a method to make liquid chemicals, such as functional intermediates, solvents, and liquid fuels from biomass-derived cellulose. The method is cascading; the product stream from an upstream reaction can be used as the feedstock in the next downstream reaction. The method includes the steps of deconstructing cellulose to yield a product mixture comprising levulinic acid and formic acid, converting the levulinic acid to γ-valerolactone, and converting the γ-valerolactone to pentanoic acid. Alternatively, the γ-valerolactone can be converted to a mixture of n-butenes. The pentanoic acid so formed can be further reacted to yield a host of valuable products. For example, the pentanoic acid can be decarboxylated yield 1-butene or ketonized to yield 5-nonanone. The 5-nonanone can be hydrodeoxygenated to yield nonane, or 5-nonanone can be reduced to yield 5-nonanol. The 5-nonanol can be dehydrated to yield nonene, which can be dimerized to yield a mixture of $C_9$ and $C_{18}$ olefins, which can be hydrogenated to yield a mixture of alkanes. Alternatively, the nonene may be isomerized to yield a mixture of branched olefins, which can be hydrogenated to yield a mixture of branched alkanes. The mixture of n-butenes formed from γ-valerolactone can also be subjected to isomerization and oligomerization to yield olefins in the gasoline, jet and Diesel fuel ranges.

9 Claims, 21 Drawing Sheets

OTHER PUBLICATIONS

West et al., Liquid Alkanes with Targeted Molecular Weights from Biomass-Derived Carbohydrates, *ChemSusChem* (2008) 1, 417-424.

Zhu, et.al., Dissolution of cellulose with ionic liquids and its application: a mini-review, *Green Chem.* 8, 325-327 (2006).

Heeres, Hans, et al., Combined dehydration/(transfer)-hydrogenation of C6-sugars (D-glucose and D-fructose) to γ-valerolactone using ruthenium catalysts, Green Chem., 2009, 11, 1247-1255.

Gao, Yuan, et al., The interconversion of formic acid and hydrogen/carbon dioxide using a binuclear ruthenium complex catalyst, J. Chem. Soc., Dalton Trans., 2000, 3212-3217.

Huber, George W., et al., Synthesis of Transportation Fuels from Biomass: Chemistry, Catalysts, and Engineering, Chem. Rev. 2006, 106, 4044-4098.

\* cited by examiner

US 8,148,553 B2

CATALYTIC CONVERSION OF CELLULOSE TO LIQUID HYDROCARBON FUELS BY PROGRESSIVE REMOVAL OF OXYGEN TO FACILITATE SEPARATION PROCESSES AND ACHIEVE HIGH SELECTIVITIES

This invention was made with United States government support awarded by the following agency: U.S. Department of Energy, Grant Number DE-FG02-03ER15468. The United States government has certain rights in this invention.

BACKGROUND

Significant advances have been made in recent years with respect to using heterogeneous catalysts for converting biomass-derived compounds to fuels and chemicals (Kunkes (2008), Chheda (2007), Huber (2007), C. H. Christensen (2008)). These studies deconstruct solid cellulose into smaller molecules that are soluble in various solvents (e.g., water, ionic liquids), thereby allowing transport of these reactants to the active sites on the heterogeneous catalyst, the majority of which are located within the pores of a high-surface area material (Robinson (2004), Zhu (2006)). A difficulty in implementing this strategy is that chemical components used to deconstruct solid cellulose (e.g., sulfuric acid) may alter the performance of heterogeneous catalysts used subsequently to convert the soluble biomass-derived reactants to the desired fuels and/or chemicals. As a result, costly purification steps are required to implement a cascade catalytic process. The present invention is a cascading method to convert cellulose to liquid fuels that addresses this long-felt and unmet need.

SUMMARY OF THE INVENTION

A first version of the invention is directed to a method for converting cellulose to pentanoic acid. The first version of the method comprises deconstructing biomass comprising cellulose to yield a product mixture comprising levulinic acid and formic acid. The levulinic acid is then converted to γ-valerolactone (GVL). The γ-valerolactone is then converted to pentanoic acid (PAA). It is preferred that the biomass-derived cellulose is deconstructed by reacting it with an acid, preferably an acid selected from the group consisting of sulfuric acid, hydrochloric acid, nitric acid, phosphoric acid, boric acid, hydrofluoric acid, hydrobromic acid, oxalic acid, acetic acid, acetic anhydride, and combinations thereof, and most preferably sulfuric acid.

Converting the levulinic acid to γ-valerolactone may be accomplished by contacting the levulinic acid with a heterogeneous catalyst comprising a metal selected from the group consisting of Fe, Co, Ni, Ru, Rh, Pd, Os, Ir, Pt, Ag, Au, and combinations thereof. It is preferred that the levulinic acid is converted to γ-valerolactone by contacting the levulinic acid with a heterogeneous catalyst comprising Ru/C. Converting the γ-valerolactone to pentanoic acid is preferably accomplished by contacting the γ-valerolactone with a catalyst comprising a metal selected from the group consisting of Ti, V, Cr, Zr, Nb, Mo, Hf, Ta, W, Pd, Ag, Pt, Au, and combinations thereof, in the presence of hydrogen. The preferred catalyst for converting the γ-valerolactone to pentanoic acid is a catalyst comprising a combination of Nb and Pd.

It is preferred, although not required, that the γ-valerolactone formed in the inventive process is separated from the acidic reaction medium by extracting it into a polar, aprotic solvent, such as ethyl acetate, methyl acetate, acetone, dimethyl ether, diethyl ether, acetonitrile, tetrahydrofuran, and the like (either neat or in a solvent system comprising one or more polar, aprotic solvents). Ethyl acetate is preferred.

In another version of the invention, the pentanoic acid formed as described herein is decarboxylated to yield a product mixture comprising n-butenes, including 1-butene, a valuable alpha-olefin feedstock. 1-butene (CAS No. 106-98-9) is a high-volume monomer, with production exceeding 1 million pounds per year in the US (data from the American Chemical Society). It is easily polymerized using Ziegler-Natta catalysts, to yield poly(butylene).

Another version of the present method is directed to method for converting cellulose to liquid fuels. The method comprises the steps noted earlier, namely: deconstructing biomass comprising cellulose to yield a product mixture comprising levulinic acid and formic acid; converting the levulinic acid to γ-valerolactone; and converting the γ-valerolactone to pentanoic acid. In this version, however, the pentanoic acid is then ketonized to yield 5-nonanone. The 5-nonanone so formed is useful in its own right as a solvent and fuel additive. The 5-nonanone can also be further manipulated to yield a host of valuable solvents, fuels, and fuel additives. For example, the 5-nonanone can be hydrodeoxygenated to yield nonane. Alternatively, the 5-nonanone can be reduced to yield 5-nonanol. The 5-nonanol so formed can be dehydrated to yield nonene. The nonene can be dimerized to yield a mixture of $C_9$ and $C_{18}$ olefins. The mixture of $C_9$ and $C_{18}$ olefins can be hydrogenated to yield a mixture of alkanes.

Alternatively, the nonene formed as described above can be isomerized to yield a mixture of branched olefins. If this version is used, hydrogenating the mixture of branched olefins yields a mixture of branched alkanes. Both the olefins and the alkanes are useful as fuel additives in gasoline, jet fuel, and Diesel.

Another version of the invention is directed to a method for converting glucose to γ-valerolactone. The glucose reactant may be derived from any source, without limitation, but is preferably derived from biomass (i.e., plant material, vegetation, agricultural waste, as well as cellulose-containing consumer, commercial, and industrial waste). The method comprises hydrolyzing glucose derived from any source in an aqueous, acid-catalyzed reaction to yield a product mixture comprising levulinic acid and formic acid, and then converting at least a portion of the formic acid present in the product mixture to $H_2$ and $CO_2$ without separating the levulinic acid and formic acid present in the product mixture. At least a portion of the levulinic acid present in the product mixture is reduced to γ-valerolactone using the $H_2$ produced from the formic acid. The glucose may be hydrolyzed by reacting it with an acid, such as (by way of example and not limitation) sulfuric acid, hydrochloric acid, nitric acid, phosphoric acid, boric acid, hydrofluoric acid, hydrobromic acid, oxalic acid, acetic acid, acetic anhydride, and combinations thereof.

Converting the formic acid present in the product mixture to $H_2$ and $CO_2$ can be accomplished by contacting the product mixture with a heterogeneous catalyst comprising a metal selected from the group consisting of Fe, Co, Ni, Ru, Rh, Pd, Os, Ir, Pt, Ag, Au, and combinations thereof. A catalyst comprising ruthenium on a support is preferred.

The γ-valerolactone so formed may be concentrated by extracting it into a solvent comprising a polar, aprotic solvent; or by evaporating the γ-valerolactone so formed.

The γ-valerolactone may then be converted to any number of valuable products, including pentanoic acid and n-butenes. Converting the γ-valerolactone to pentanoic acid can be accomplished by contacting the γ-valerolactone with a catalyst comprising a metal selected from the group consisting of Ti, V, Cr, Zr, Nb, Mo, Hf, Ta, W, Pd, Ag, Pt, Au, and combinations thereof, in the presence of hydrogen. A catalyst comprising Nb and Pd is preferred.

To make 1-butene, at least a portion of the γ-valerolactone can be decarboxylated by contacting it with a solid acid catalyst, to yield a product mixture comprising 1-butene. The γ-valerolactone can also be decarboxylated by reacting it with a mineral acid selected from the group consisting of sulfuric acid, hydrochloric acid, nitric acid, phosphoric acid, boric acid, hydrofluoric acid, hydrobromic acid, acetic acid, acetic anhydride, oxalic acid, and combinations thereof. Decarboxylating the γ-valerolactone can also be accomplished by reacting it with a heterogeneous catalyst comprising a metal selected from the group consisting of Fe, Co, Ni, Ru, Rh, Pd, Os, Ir, Pt, Ag, Au, Ru and combinations thereof.

All percentages, parts and ratios used herein are by weight of the total composition, unless otherwise specified. All such weights as they pertain to listed ingredients are based on the active level and, therefore, do not include solvents or by-products that may be included in commercially available materials, unless otherwise specified.

The catalysts described herein may be used without a support or disposed on an inert or catalytically active support. Any catalyst support now known or developed in the future, without limitation, may be used. Suitable supports include carbon in any form (including nano-particles, "buckyballs," single and multi-wall nanotubes, etc.), silica, titania, alumina, silica/alumina, zirconia, etc., in any form (e.g., spheres, tablets, Raschig rings, and the like), zeolites, etc.

Solid acid catalysts may be used in the present method, including any ceramic acid or acidic molecular sieve such as an acidic zeolite, an aluminosilicate, a titanosilicate, a borosilicate, any mixed oxide such as tungstated zirconia, any phosphated or sulphated catalyst such as sulphated or phosphated metal oxide, or a phosphate or sulphuric acid catalyst such as niobium phosphate, any heteropoly acid and any acidic ion exchange resin, as well as any combination or subset of these supported on inert materials such as carbon.

When homogeneous catalysts are used, it is preferred that residual homogenous catalyst from any earlier step in the method is present in a concentration of between 0 and about 2 M, more preferably between 0 and about 0.5 M, and more preferably still between 0 and about 0.1 M.

The various reactions may be conducted under a host of temperature, pressure, and WHSV ranges. While not being limited to these ranges, it is preferred that the various reactions described herein be conducted at a temperature range of from about 300 K to about 1100 K, more preferably from about 350 K to about 800 K, and more preferably still from about 400 K to about 600 K. Reaction temperatures above and below these stated ranges are explicitly within the scope of the method claimed herein. The reactions are preferably conducted at pressures ranging from about 0.1 bar to about 300 bar, more preferably from about 1 bar to about 20 bar, and most preferably from about 1 bar to about 5 bar. Reaction pressures above and below these stated ranges are explicitly within the scope of the method claimed herein. The reactions are preferably conducted at a WHSV of from about 0.1 to about 50 h$^{-1}$, more preferably from about 0.1 to about 30 h$^{-1}$, and most preferably from about 0.1 to about 10 h$^{-1}$. WHSVs above and below these stated ranges are explicitly within the scope of the method claimed herein.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

BRIEF DESCRIPTION OF THE DRAWINGS

FIG. 3A: Pd(5%)/Nb$_2$O$_5$ at 548 K, 14 bar, WHSV=0.5 h$^{-1}$, feed: 30 wt % GVL in water 0.02 M H$_2$SO$_4$. FIG. 3B: Pd(5%)/Nb$_2$O$_5$ at 548 K, 14 bar, WHSV=0.3 h$^{-1}$, feed: 40 wt % GVL in water 0.04 M H$_2$SO$_4$. FIG. 3C: Pd(5%)/Nb$_2$O$_5$+Ce$_{0.5}$Zr$_{0.5}$O$_2$ at 598

K-698 K, 14 bar, WHSV=0.8 h$^{-1}$–0.5 h$^{-1}$, feed: 40 wt % GVL in water 0.02 M H$_2$SO$_4$. FIG. 3D: Pd(5%)/Nb$_2$O$_5$ at 598 K, 1 bar, WHSV=0.3 h$^{-1}$, feed: 40 wt % GVL in water 0.02 M H$_2$SO$_4$.

DETAILED DESCRIPTION OF THE INVENTION

The present method is a cascading catalytic process for converting glucose derived from any source (but preferably from biomass-derived cellulose) to pentanoic acid and subsequently to 5-nonanone and other downstream products. 5-Nonanone is a C$_9$-ketone that serves as a precursor for producing gasoline, jet and Diesel fuels by catalytic upgrading strategies, e.g., reactions involving hydrogenation, dehydration, isomerization, and oligomerization steps. In the present method, many purification and complex separation steps conventionally used to convert cellulose into liquid fuels are eliminated by steering the catalytic chemistry for carbohydrate conversion to produce hydrophobic intermediates that separate spontaneously (or can be easily extracted) from the aqueous reaction media. The first of these intermediates, GVL, is separated very effectively and efficiently from a sulfuric acid reaction media using ethyl acetate. The second and third of these intermediates, pentanoic acid and 5-nonanone, separate spontaneously from aqueous solutions and are valuable intermediates for producing chemicals and liquid transportation fuels.

Figure 1:
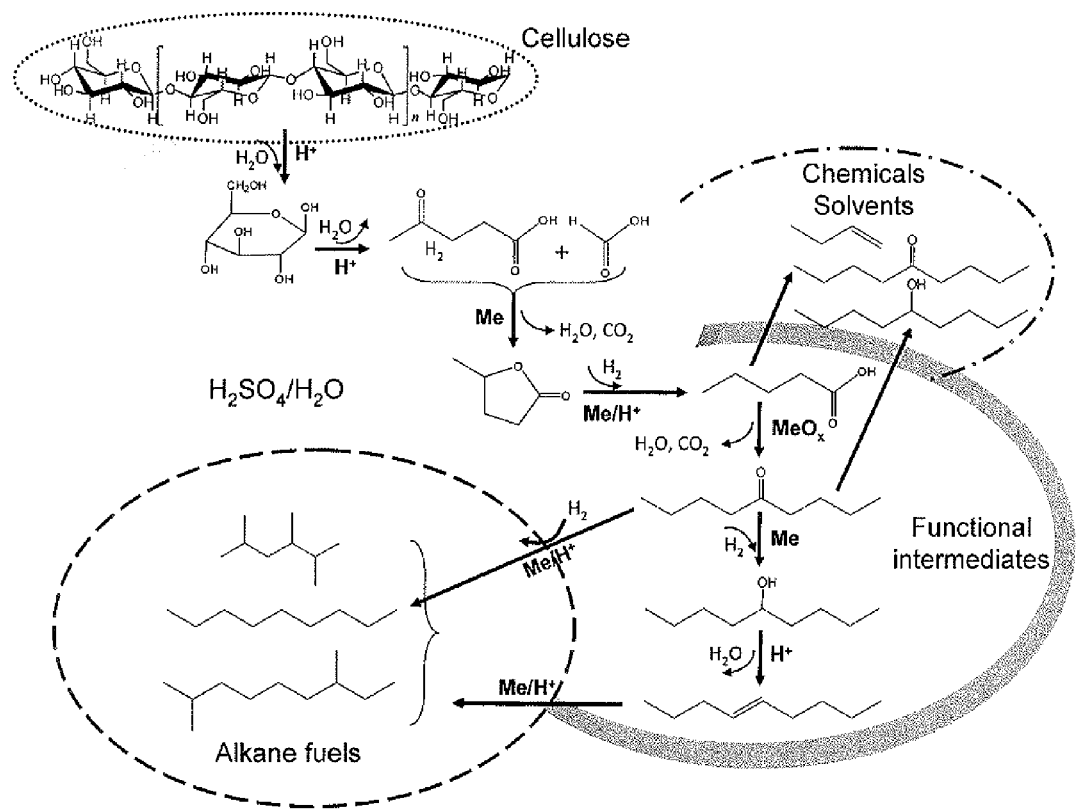
FIG. 1 depicts a strategy according to the subject method for converting solid cellulose to chemical intermediates (e.g., pentanoic acid, 5-nonanone, etc.) and/or producing liquid alkane fuels from functional intermediates. Solid cellulose (dotted outline) undergoes acid-catalyzed (H+) deconstruction in an aqueous solution of sulfuric acid (light grey), followed by conversion over a metal catalyst (Me) to γ-valerolactone (GVL) and further conversion over a bi-functional catalyst containing metal and acid sites (Me/H+) to pentanoic acid, which separates spontaneously to form an organic liquid (dark grey). Pentanoic acid can undergo ketonization over a metal oxide catalyst (MeOx) to form 5-nonanone, the latter of which can be converted to liquid fuels (dashed outline). For example, 5-nonanone can be converted to nonane over a bi-functional catalyst containing metal and acid sites (Me/H+). Alternatively, 5-nonanone can be converted to nonanol over a metal catalyst (Me), followed by dehydration to nonene combined with isomerization and/or oligomerization over an acid catalyst (H+), and completed by hydrogenation over a metal catalyst (Me). Chemicals and solvents (dashed-dotted outline) can also be produced from cellulose by using 5-nonanone and 5-nonanol, and/or by converting pentanoic acid to 1-butene by decarboxylation.

The general approach of the method for converting cellulose to chemicals and/or fuels is outlined in FIG. 1. In a first step, an acid catalyst (for example, sulfuric acid, hydrochloric acid, nitric acid, phosphoric acid, boric acid, hydrofluoric acid, hydrobromic acid, acetic acid, acetic anhydride, etc.) in water is used to deconstruct solid cellulose by hydrolysis to yield an aqueous solution of glucose. Sulfuric acid and hydrochloric acid are preferred. The glucose is then dehydrated in an acid-catalyzed reaction to yield levulinic acid and formic acid. A heterogeneous catalyst (preferably Ru/C) is then used to convert formic acid to H$_2$ and CO$_2$. The H$_2$ so formed is used to reduce levulinic acid to GVL. The GVL product is both more hydrophobic than levulinic acid and boils at a lower temperature. This permits selective separation of the GVL from the aqueous mineral acid reaction solution. Most of the acid can be recycled back to the cellulose deconstruction reactor. An aqueous solution of GVL containing smaller amounts of acid is then passed over another catalyst (preferably Pd/niobia) in the presence of H$_2$ to yield pentanoic acid. This takes place via a combination of ring-opening and hydrogenation reactions over catalytic sites associated with niobia and Pd, respectively. The pentanoic acid so formed can subsequently be converted to 5-nonanone by ketonization over a suitable catalyst, preferably ceria/zirconia. (See C. Gaertner et al (2009) and M. Renz (2004) for general descriptions of ketonization reactions.) A key advantage of the subject method is that the hydrophobic pentanoic acid and 5-nonanone products spontaneously separate from water, thus greatly simplifying the purification of the desired products produced from cellulose.

As shown further in FIG. 1, the liquid stream of 5-nonanone can be used for chemical applications, or it can be processed further to produce a variety of transportation fuel components. For example, 5-nonanone can undergo hydrodeoxygenation over a bi-functional catalyst containing metal and acid sites (R. West (2008)) to produce nonane for use in jet and Diesel fuel. 5-Nonanone can also be reduced to 5-nonanol over a metal catalyst for use in other chemical applications, followed by dehydration over an acid catalyst to produce nonene. This stream of nonene can undergo skeletal isomerization over an acid catalyst to produce branched olefins (or alkanes following hydrogenation) for use in gasoline (J. Abbot (1987)). Another option is to dimerize nonene over an acid catalyst to produce a mixture of $C_9$ and $C_{18}$ olefins (or alkanes following hydrogenation) for use as heavier components in jet and Diesel fuels (Arno de Klerk (2005)). In addition to the aforementioned applications for transportation fuels, pentanoic acid can undergo catalytic decarboxylation to 1-butene (J. Miller (1993), see Examples), providing a strategy for using cellulose to produce α-olefins for the polymer industry.

An important aspect in converting cellulose to pentanoic acid and 5-nonanone is managing the mineral acid (preferably sulfuric acid) used in the cellulose deconstruction step. The preferred catalyst (Ru/C) used to convert levulinic acid and formic acid to GVL and $CO_2$ operates effectively in the presence of sulfuric acid. The sulfuric acid itself is not consumed during this catalytic step. The preferred palladium-based catalyst used to convert GVL to pentanoic also operates in the presence of sulfuric acid. However, the palladium-based catalyst reduces sulfuric acid to $H_2S$. Therefore, it is desirable, but not required, to remove a significant fraction of the sulfuric acid from the aqueous solution after converting levulinic acid to GLV, and prior to converting the GVL to pentanoic acid. This minimizes the amount of $H_2S$ that must be removed from the $H_2$ gas stream (e.g., by scrubbing). At the same time, most of the sulfuric acid can be recycled back to the cellulose deconstruction reactor.

Two scenarios have been explored for partially removing (and recycling) the sulfuric acid from the aqueous solution of GVL (see the Examples for full details). In one approach, ethyl acetate is used to extract GVL from the aqueous solution of GVL and sulfuric acid. In particular, when equal masses of ethyl acetate and the aqueous solution are contacted at room temperature, approximately 76% of the GVL and only 3% of the sulfuric acid are extracted into the organic solvent (see Table 2 in the Examples). In this respect, converting levulinic acid to GVL represents an important processing step because it yields a more hydrophobic species (GVL) that is more effectively extracted by an organic solvent. The aqueous solution containing sulfuric acid (and small amounts of GVL) is then recycled back to the cellulose deconstruction reactor. (The GVL in the recycled acid stream is inert during subsequent rounds of cellulose deconstruction.) The organic fraction containing GLV undergoes further catalytic processing following removal of the ethyl acetate solvent in an evaporator. Importantly, the heat required to vaporize the ethyl acetate solvent amounts to only 14% of the heat required to vaporize an equal mass of water. This is a result of the higher molecular weight and lower heat of vaporization for ethyl acetate. By extracting the GVL into ethyl acetate, a huge amount of energy is saved as compared to evaporating the aqueous solvent to concentrate the GVL.

In a second approach for managing the acid used to deconstruct the cellulose, the aqueous solution of GVL and sulfuric acid is fed along with gaseous $H_2$ (at a $H_2$:GVL molar ratio of from about 2:1 to about 10:1) to a vapor-liquid separator operating at a targeted temperature and pressure to produce a gas stream consisting primarily of water and GVL, with small amounts of sulfuric acid, and a liquid stream consisting primarily of sulfuric acid and small amounts of GVL. This separator takes advantage of the higher boiling point of sulfuric acid compared to GVL and water. A gas-liquid separator operating at 14 bar and a temperature near 473 K leads to a gas stream containing $H_2$, water and 80% of the GLV, with only about 15% of the sulfuric acid (see the Examples and FIGS. 7 and 8). This gas stream may then optionally undergo further catalytic processing, and the liquid stream containing the remainder of the GVL and 85% of the sulfuric acid is recycled back to the cellulose deconstruction reactor. In this approach, converting levulinic acid to GVL is beneficial in view of the lower boiling point of GVL compared to levulinic acid, leading to more effective separation from sulfuric acid, which boils at a higher temperature.

Figure 2A:
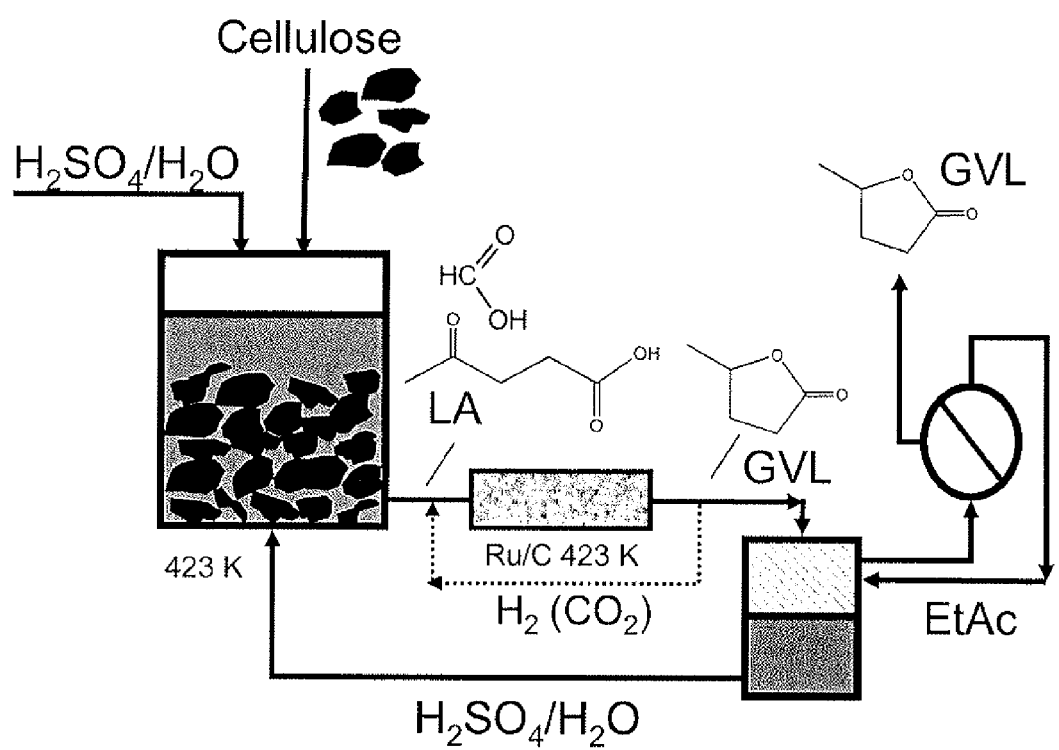
FIG. 2A depicts a cascade approach for converting cellulose to GVL and using ethyl acetate (EtAc) to extract GVL from the aqueous solution of sulfuric acid ($H_2SO_4$). Levulinic acid (LA) is formed as an intermediate.
Figure 2B:
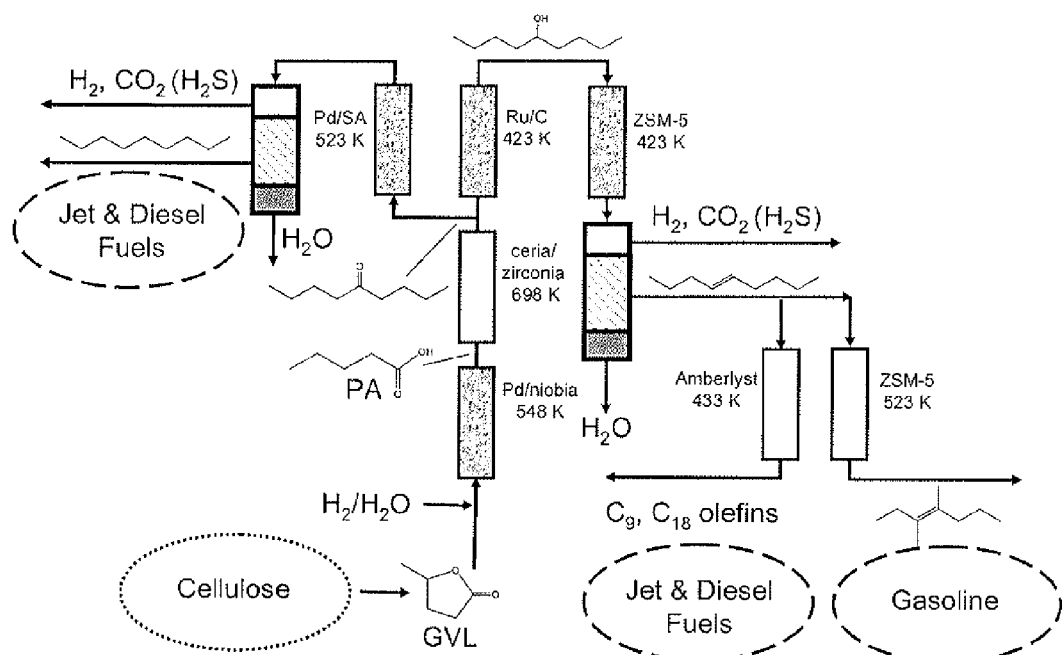
FIG. 2B depicts a cascade approach for converting GVL obtained from cellulose (as depicted in FIG. 2A) to pentanoic acid (PA), then 5-nonanone, and subsequently to nonane or nonanol, taking advantage of the spontaneous separation of nonane and nonanol from water. The liquid stream of nonane can be used in jet and Diesel fuels. The liquid stream of nonanol can be converted by dehydration to $C_9$ olefins (for use in gasoline) or to a mixture of $C_9$ and $C_{18}$ olefins (for use in jet and Diesel fuels) by dehydration combined with dimerization.

FIGS. 2A and 2B illustrate the cascading nature of the present method for converting solid cellulose to various products, such as nonane, nonanol, $C_9$ olefins, or a mixture of $C_9$ and $C_{18}$ olefins. Of particular utility is that the effluent stream from one reactor is simply utilized as an inlet stream to a subsequent reactor without the need for an intervening complex separation step. The only separation required is a spontaneous separation of the effluent stream into multiple phases. The appropriate phase is then passed onto the next reaction in the cascade. This cascading approach for converting cellulose involves a limited number of processing steps, thereby minimizing capital costs of the process, while achieving high yields of $C_9$-products. Accordingly, it is anticipated that the present method will be employed at regional facilities to convert cellulose to $C_9$-products. By processing cellulose on a regional basis, transportation costs are minimized. Biomass is a low density product; shipping it vast distances prior to processing is not economically efficient. In stark contrast, the $C_9$ liquid product stream contains more that 90% of the energy content of the cellulose feedstock, but less than 35% of the mass of the cellulose feedstock. Thus, $C_9$ liquid product could be economically shipped to more centrally located facilities for subsequent processing to the final fuel and/or chemical products.

The schematic process flow-sheet shown in FIG. 2A shows a first version of a method that uses the extraction strategy outlined above (employing ethyl acetate, EtAc, as a solvent) to separate and recycle sulfuric acid from GVL. As shown in FIG. 2A, an aqueous solution of sulfuric acid (e.g., 0.5 M) at 423 K is used to hydrolyze cellulose to an equi-molar mixture of levulinic acid and formic acid. A carbon-supported ruthenium catalyst at 448 K is then employed to convert the formic acid in this solution to $CO_2$ and $H_2$. The $H_2$ so formed reduces levulinic acid to GVL, a conversion that requires one mole of $H_2$ per mole of levulinic acid (see the Examples and FIG. 6). In this fashion, the $H_2$ released by the decomposition of formic acid is utilized in the catalytic reduction of levulinic acid. To ensure that that the ruthenium catalyst remains in the metallic state, an optional $H_2$ recycle stream is shown in FIG. 2A (including $CO_2$ removal). The $H_2$ recycle loop ensures a constant presence of $H_2$ within the catalytic reaction chamber. The aqueous solution of GVL containing sulfuric acid is then contacted with ethyl acetate, leading to extraction of most of the GVL into the organic phase (yellow), and retention of the most of the sulfuric in the aqueous phase. The aqueous phase is then recycled back to the cellulose deconstruction reactor. The organic stream containing GVL and small amounts of sulfuric acid is sent to an evaporator, from which the ethyl acetate solvent is condensed and recycled back to the separator for further extraction of GVL.

Figure 3A:
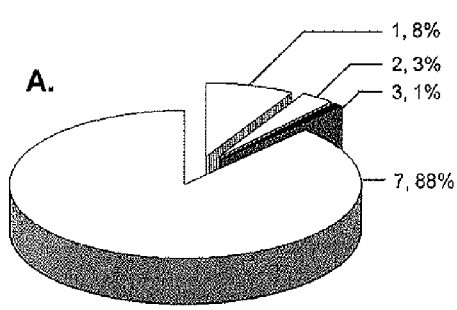
FIGS. 3A, 3B, 3C, and 3D are pie charts depicting % carbon composition (carbon %) of the organic layer obtained after various reactions according to the present method. The component numbering corresponds to $C_4$-$C_5$ alkanes (1), pentanal/pentanol (2), esters (3), 5-nonanone (4), $C_6$-$C_7$ ketones (5), GVL (6) and pentanoic acid (7).
Figure 3B:
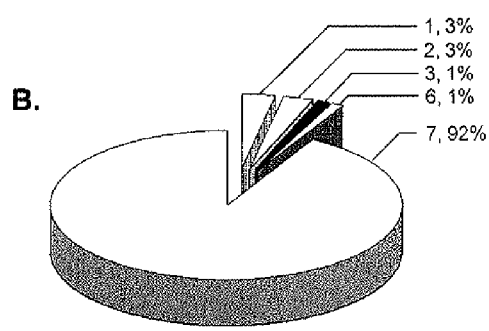
Figure 3C:
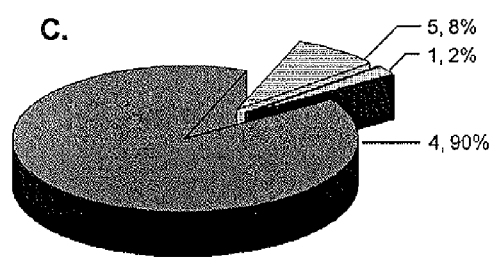

As shown in FIG. 2B, the liquid GVL stream from the evaporator is then sent with $H_2$ to a Pd/niobia catalyst operating at 548 K, over which the GVL is further reduced to pentanoic acid, followed by conversion over ceria/zirconia at 698 K to produce 5-nonanone by ketonization. Optionally, water may be added to the GVL reactant stream to eliminate formation of carbonaceous deposits on the Pd/niobia catalyst. Table 1 summarizes results (carbon distribution and carbon selectivities) for the catalytic conversion of aqueous solutions of GVL (30-40 wt %) with different acid concentrations (0.02 to 0.04 M) over Pd(5%)/Nb$_2$O$_5$. (More extensive results are presented in the Examples, see Table 3.) The ranges of GVL and acid concentrations described here and in the Examples are typical of those obtained after the two strategies described herein to remove acid from the solution produced by cellulose deconstruction. It can be seen that GVL is selectively converted to pentanoic acid over Pd(5%)/Nb$_2$O$_5$ for all ranges of acid and feed concentrations tested. Importantly, the pentanoic acid accumulates in an organic layer that spontaneously separates from water and accounts for approximately 95% of the carbon fed to the reactor. The main byproducts formed are butane (produced by decarboxylation of pentanoic acid, with stoichiometric amounts of CO$_N$), pentanal/1-pentanol/pentane (produced by successive hydrogenations of pentanoic acid), and the ester pentyl pentanoate (produced by esterification between pentanoic acid and 1-pentanol). The organic layer produced is rich in pentanoic acid, with minor amounts of pentanal/1-pentanol, traces of pentyl pentanoate, unreacted GVL, and small amounts of butane and pentane dissolved in the oil as a consequence of the pressure of the system (see FIGS. 3A and 3B). Remarkably, no carbon is present in the aqueous phase (see Table 1), thus allowing the recycling of this water in the process. The carbon selectivity toward pentanoic acid is approximately 90% in all cases, except for the solution containing 30 wt % GVL-0.02 M H$_2$SO$_4$ (Table 1, entry 1) in which the yield (78%) and the amount of carbon stored in the organic layer (87%) decreased because of the formation of gaseous butane and pentane (16%). However, decreasing the reaction temperature (see Table 3, entry 1) and the space velocity (Table 3, entry 2), yields selectivities to pentanoic acid near 90% for this specific feedstock. Interestingly, an increase in the acid concentration from 0.02 to 0.04 M slightly decreases the conversion of the 30 wt % GVL solution (from 100 to 94%, entries 1-3), while producing an increase in the selectivity to pentanoic acid (from 78 to 89%) by controlling the activity of the metal in the hydrogenation and decarboxylation processes. In the case of the 40 wt % GVL feed, it was necessary to decrease the space velocity (only 84% conversion at 0.7 h$^{-1}$, entry 3 of Table 3) by a factor of 2 to achieve nearly complete conversion of the reactant. Similar results were obtained for carbon distribution and carbon selectivities for all the acid concentration ranges (Table 1, entries 4-7). FIG. 2B illustrates another version of the present method for direct production of 5-nonanone from aqueous acid solutions of GVL by using a second bed of ceria-zirconia in a cascade mode. As seen in Table 1, entry 7, a 40 wt % GVL aqueous solution with a sulfuric acid concentration of 0.02 M can be efficiently converted to an organic stream (accounting for almost 90% of the carbon fed) that is rich in 5-nonanone over a Pd(5%)/Nb$_2$O$_5$+Ce$_{0.5}$Zr$_{0.5}$O$_2$ double bed arrangement (see FIG. 3C), with good stability versus time-on-stream (See also the Examples and FIG. 10). 5-Nonanone is produced along with stoichiometric amounts of CO$_2$. If the CO$_2$ is included in the calculations, the C$_9$ ketone is generated with almost 90% selectivity (Table 1). The main by-products of the process are 2-hexanone and 3-heptanone, produced by scission of 5-nonanone at the alpha and beta positions, respectively. These by-products also accumulate in the organic layer (see FIG. 3C). Importantly, their presence would not affect the subsequent processes of the cascade approach depicted in FIG. 2B because they form olefins in the gasoline range. 2-Hexanone and 3-heptanone can also be oligomerized to produce C$_{12}$-C$_{14}$ alkanes that fall within the jet and Diesel fuel ranges. The preferred ceria-zirconia bed was operated at a higher temperature (698 K) than Pd(5%)/Nb$_2$O$_5$ (548 K) to achieve complete conversion of the pentanoic acid formed in the first bed (see Table 3, entries 7 and 8). This stream of 5-nonanone can be converted at 523 K to nonane for use in jet and Diesel fuels by hydrogenation combined with dehydration over a bi-functional catalyst containing metal (e.g., Fe, Co, Ni, Ru, Rh, Pd, Os, Ir, Pt, Ag, Au, and combinations thereof) and acid sites (e.g., silica-alumina, etc.) (Huber (2007), West (2008)). Alternatively, the stream of 5-nonanone can undergo hydrogenation over a Ru/C catalyst operating at 423 K to produce 5-nonanol, followed by dehydration over an acid catalyst at 423 K (e.g., ZSM-5) to produce nonene. Importantly, all of these C$_9$ compounds spontaneously separate from water. The water may then be recycled back to the GVL stream entering the reactor containing the Pd/niobia catalyst. The liquid stream of linear nonene undergoes isomerization over a zeolite catalyst (e.g., ZSM-5 at 523 K) to produce branched C$_9$-olefins (or alkanes upon subsequent hydrogenation) for use as gasoline components. Alternatively, nonene undergoes dimerization over an acid catalyst (e.g., "AMBERLYST"-brand catalysts at 433 K) to produce a mixture of C$_9$ and C$_{18}$ olefins (or alkanes upon subsequent hydro-

TABLE 1

Reaction kinetics results for the conversion of aqueous solutions of GVL and sulfuric acid to produce pentanoic acid and 5-nonanone over Pd(5%)/Nb$_2$O$_5$.

| Entry | Catalyst | Feed | T (K)/P (bar)/ WHSV (h$^{-1}$) | GVL Conversion (%) | C distribution (%) | | | | C$_9$=O (+stoich. CO$_2$) | C selectivity (%) | | | |
|---|---|---|---|---|---|---|---|---|---|---|---|---|---|
| | | | | | Aq | Org | Gas | PA (Ester) | | CO$_x$ | C$_4$+C$_5$ Alkanes | Pentanal/ 1-Pentanol | C$_6$-C$_7$ Ketones |
| 1 | Pd(5%)/Nb$_2$O$_5$ | 30% GVL-0.02 M H$_2$SO$_4$ | 548/14/0.5 | 100 | — | 87 | 13 | 78 (1) | — | 2 | 16 | 3 | — |
| 2 | Pd(5%)/Nb$_2$O$_5$ | 30% GVL-0.03 M H$_2$SO$_4$ | 548/14/0.5 | 98 | — | 94 | 6 | 87 (1) | — | 1 | 9 | 2 | — |
| 3 | Pd(5%)/Nb$_2$O$_5$ | 30% GVL-0.04 M H$_2$SO$_4$ | 548/14/0.5 | 94 | 1 | 94 | 5 | 89 (—) | — | 1 | 8 | 2 | — |
| 4 | Pd(5%)/Nb$_2$O$_5$ | 40% GVL-0.04 M H$_2$SO$_4$ | 548/14/0.3 | 99 | — | 94 | 6 | 88 (1) | — | 1 | 8 | 2 | — |
| 5 | Pd(5%)/Nb$_2$O$_5$ | 40% GVL-0.03 M H$_2$SO$_4$ | 548/14/0.3 | 98 | — | 95 | 5 | 88 (1) | — | 1 | 7 | 3 | — |
| 6 | Pd(5%)/Nb$_2$O$_5$ | 40% GVL-0.02 M H$_2$SO$_4$ | 548/14/0.3 | 98 | — | 95 | 5 | 88 (1) | — | 1 | 7 | 3 | — |
| 7 | Pd(5%)/Nb$_2$O$_5$ Ce$_{0.5}$Zr$_{0.5}$O$_2$ | 40% GVL-0.02 M H$_2$SO$_4$ | 548/14/0.8 698/14/0.5 | 100 | — | 89 | 11 | — | 80 (89) | 9 | 4 | — | 7 | genation) for use in jet and Diesel fuels. ("AMBERLYST" is a registered trademark of Rohm & Haas Company, a wholly owned subsidiary of Dow Chemical Company.)

It is not generally advantageous to process dilute liquid solutions, because of the larger reactor volumes required to handle the larger amounts of solvent (e.g., water in this case). In this respect, the present method achieved elevated levels of levulinic acid in water (e.g., 20 wt %) at 423 K by adding solid cellulose to the aqueous solution of sulfuric acid (0.5 M) in the reactor at various stages of the deconstruction step. In particular, the levulinic acid yield is above 60% for the first cycle and gradually decreases with each cycle of cellulose addition, such that the final overall levulinic acid yield is equal to 52% after 5 cycles (see the Examples and FIG. 5). This approach avoids having high levels of cellulose in the slurry at any given time, thereby achieving effective mixing in the reactor over the entire period of deconstruction. This approach also avoids having high concentrations of glucose in the reactor at any given time, thereby minimizing undesirable polymerization reactions that lead to humins and which decrease the yield to levulinic acid (Girisuta (2007)). Importantly, this strategy is effective because the levulinic acid and formic acid products are stable and inert at the reaction conditions used for cellulose deconstruction. Thus, the products formed during the deconstruction of a given batch of cellulose do not degrade during subsequent rounds of deconstruction. Nor do the products formed interfere with or inhibit subsequent rounds of deconstruction.

The conversion of cellulose to levulinic acid using the present method was roughly 52-60%. This yield can be increased to approximately 60-65% by optimizing the reaction conditions (Girisuta (2007)). The cellulose that is not converted to levulinic acid can be burned to supply combined heat and power at locations near to the biomass growth area. Alternatively, this solid fraction can be utilized to provide heat (by combustion) and $H_2$ (by gasification) required for the processing of the levulinic fraction to liquid hydrocarbon fuels (Koppatz).

The following stoichiometric equation represents the conversion of glucose to nonane, $CO_2$ and $H_2O$:

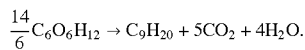

$$\frac{14}{6} C_6 O_6 H_{12} \rightarrow C_9 H_{20} + 5 CO_2 + 4 H_2 O.$$

According to the equation, 5 molecules of $CO_2$ are required for each molecule of nonane produced. Converting two glucose molecules to levulinic acid produces two moles of $CO_2$. Ketonization of two molecules of pentanoic acid produces one molecule of $CO_2$. It is therefore necessary to produce two additional molecules of $CO_2$ from biomass to provide the hydrogen necessary to complete the conversion of cellulose to nonane. Thus, in the stoichiometric equation above, the production of nonane utilizes 12 carbon atoms from cellulose via formation of levulinic acid and 2 carbon atoms from cellulose via formation of $H_2$ and $CO_2$. The $CO_2$ corresponds to 14% of the cellulose conversion. Assuming the yield of levulinic acid from glucose to be approximately 55%, 55% of the carbon in the cellulose feed would be converted to hydrocarbons (plus a stoichiometric amount of $CO_2$) through levulinic acid; 15% of the carbon would be required for producing $H_2$ (plus a stoichiometric amount of $CO_2$) required to complete the stoichiometry of the overall reaction shown above; and 30% of the carbon would be available for other purposes, such as providing process heat for the overall conversion of cellulose to liquid alkanes, or undergoing conversion by gasification or pyrolysis.

Figure 3D:
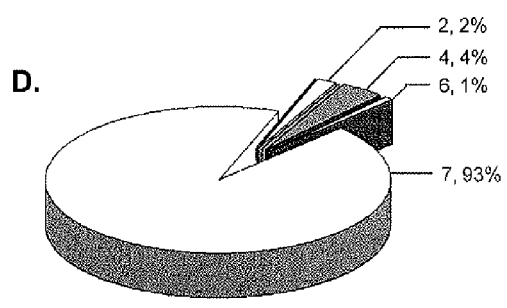

Synergies may be achieved by coupling biomass gasification with the present process for converting cellulose to pentanoic acid, 5-nonanone, and/or liquid hydrocarbons. Whereas the present method produces high-value, chemical intermediates and/or liquid hydrocarbons with high selectivity from the cellulose fraction of biomass, it does not convert all of the carbon present in biomass. In contrast, biomass gasification can be employed on all components present in biomass. Because biomass-gasification processes can be carried out at atmospheric pressure, converting aqueous solutions of GVL into pentanoic acid and/or 5-nonanone at atmospheric pressure was explored. As can be seen in Table 3, entries 5-6, acid solutions of GVL can be converted to pentanoic acid with high yields over Pd(5%)/$Nb_2O_5$ at ambient pressure (although higher temperatures (598 K) were required to achieve complete conversion, see Table 3, entry 6). The organic layer obtained in this atmospheric pressure processing (FIG. 3D) was again rich in pentanoic acid (93% of the carbon in this phase) with minor amounts of the desired 5-nonanone (4%). Butane and pentane were not dissolved in the organic phase due to the low pressure.

While the process described herein is based on the cellulose-fraction of biomass, and gasification or pyrolysis would be employed to convert the lignin-fraction of biomass, several strategies are available to utilize effectively the hemi-cellulose fraction of biomass (Mamman (2008)). For example, this biomass fraction, comprising mainly xylose units, is converted primarily to furfural during the biomass deconstruction step. The furfural may be vaporized and thereby removed from the aqueous solution for other applications, as implemented in the Biofine process (S. W. Fitzpatrick. Patent 1990). Alternatively, the solid biomass feedstock can be subjected to an aqueous pretreatment step in which the hemicellulose fraction is hydrolyzed to produce xylose (Kumar (2009)). This aqueous solution is then used to produce $H_2$ by aqueous-phase reforming (Cortright (2002)), thereby providing $H_2$ for converting GVL to chemicals and/or fuels as described herein.

Alternatively, the xylose can be converted to mono-functional intermediates (e.g., $C_4$-$C_5$ alcohols, ketones, carboxylic acids) over Pt—Re/C catalysts (Kunkes (2008)), followed by upgrading these intermediates to targeted classes of hydrocarbons by ketonization and aldol-condensation reactions, followed by hydrodeoxygenation (Kunkes (2008)). Additionally, xylose can be selectively converted by dehydration to furfural (Chheda (2007)), which can then be used in chemical applications or can be converted to liquid fuels, such as methyltetrahydrofuran or liquid alkanes by aldol-condensation combined with hydrodeoxygenation reactions (Huber (2007), West (2008)).

Figure 4:
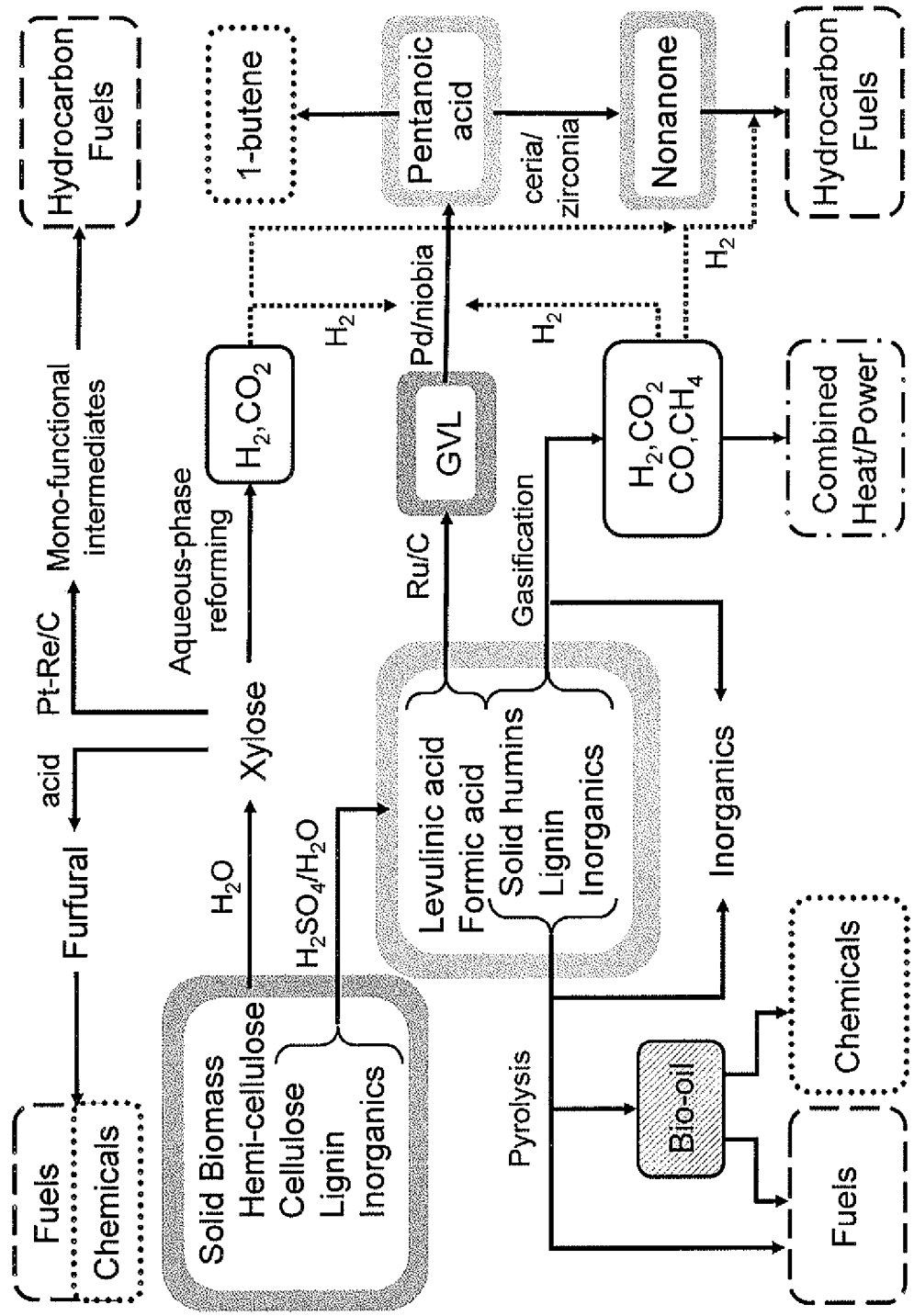
FIG. 4 is a flowchart depicting integration of levulinic processing with gasification or pyrolysis to produce fuels and chemicals from biomass. The primary cellulose conversion sequence is shown in dark grey; hemi-cellulose conversion is shown in light grey; gas-formation processes are shown in white with a solid outline; chemical intermediates are shown in white with a dashed outline; energy and fuel production are shown in white with a dotted outline.

FIG. 4 is a schematic representation of a scenario for integrating levulinic acid processing with gasification to balance hydrogen production and utilization during the production of fuels and chemicals from biomass. The hemi-cellulose fraction of biomass is used to produce $H_2$ and $CO_2$. Alternatively, this fraction is converted to furfural or mono-functional intermediates as precursors to fuels and chemicals. The cellulose fraction is used to produce GVL. Gasification is used to produce $H_2$, $CO_2$, CO and $CH_4$ from the lignin fraction and the solid humins formed during cellulose processing. The GVL intermediate is then converted to pentanoic acid using $H_2$ produced from xylose or gasification. The liquid stream of pentanoic acid can be converted to high value chemicals, such as 1-butene or 5-nonanone. The 5-nonanone can be upgraded further to liquid hydrocarbon fuels using $H_2$ produced from xylose or via gasification (see Examples). The remainder of the high heating value gas produced from xylose or gasification can be used for combined heat and power production. FIG. 4 also shows how biomass processing is accomplished by integrating levulinic acid processing with pyrolysis. In this case, the $H_2$ required for levulinic acid processing is provided by the hemi-cellulose fraction of biomass. Pyrolysis is then employed to process the lignin fraction of biomass as well as solid humins produced from converting cellulose to levulinic acid. The pyrolysis processing can be carried out to produce bio-oil, or it can be carried out with the addition of a catalyst to produce aromatic fuels (Huber).

EXAMPLES

The following Examples are included solely to provide a more complete description of the method disclosed and claimed herein. The Examples do not limit the scope of the method in any fashion.

Example 1

Analysis Method

The liquid products from the cellulose deconstruction step, the conversion of levulinic acid into GVL, and the GVL extraction step were analyzed by HPLC (Waters 2695 system with a Bio-Rad Aminex HPX-87H column and a RI 410 detector) (Waters Corp., Milford, Mass., USA; Bio-Rad Laboratories, Hercules, Calif., USA). The liquid products from the conversion of GVL into pentanoic acid and the conversion of pentanoic acid into nonanone were analyzed by GC-MS (Shimadzu GC-2010 with a mass spectrometer and DB-5ms column from Alltech) and GC (Shimadzu GC-2010 with a FID detector and Rtx-5 column from Alltech) (Shimadzu Corporation, Kyoto, Japan; Alltech Associates, Inc., Deerfield, Ill., USA). Product identification was verified using a combination of GC-MS for volatile species, and retention times for GC and HPLC. The products were purchased and calibrated for GC and HPLC.

The gas phase products from the conversion of GVL into pentanoic acid were analyzed by GC using two different gas chromatograms operating in parallel. A Shimadzu GC-8A (equipped with TCD detector and an Alltech packed column model HayeSep DB 100/120) was used to detect CO, $CO_2$ and $H_2S$. A Varian GC (Saturn 3) (Varian, Inc., Palo Alto, Calif., USA) using a FID detector and a GS-Q capillary column (Agilent Technologies, Santa Clara, Calif., USA) was used to detect other volatile organic compounds. The overall carbon balance gave recoveries ranging from 93-111%, and the sulfur balance closed to 73-111%.

Example 2

Catalyst Preparation

Pd(5%)/$Nb_2O_5$ was prepared by incipient wetness impregnation of a commercial niobium oxide (HY-340 from Companhia Brasileira de Metalurgia e Mineração (CBMM), Araxa, Brazil, BET 118 $m^2$ $g^{-1}$) with an aqueous solution of $Pd(NO_3)_2 \cdot xH_2O$ (Sigma Aldrich, Milwaukee, Wis., USA). The catalyst was dried at 380 K overnight, followed by calcination at 538 K in flowing air (250 $cm^3$(STP) $min^{-1}$, 1 K $min^{-1}$ ramp) for 2 h. The ceria-zirconia catalyst with Ce:Zr molar ratio of 1:1 was prepared according to Serrano-Ruiz, et al. (Serrano-Ruiz (2006)). A commercial Ru(5%)/C catalyst (Sigma Aldrich) was reduced at 673 K (2 K $min^{-1}$ ramp then 4 h hold) with flowing $H_2$ (100 $cm^3$(STP) $min^{-1}$) and then passivated with 2% $O_2$ in He (100 $cm^3$(STP) $min^{-1}$) at ambient temperature for 4 h prior to use in the reaction to convert levulinic acid to GVL.

Example 3

Cellulose Deconstruction to Levulinic Acid and Formic Acid

Microcrystalline cellulose (8 g, 5% moisture) with an average size of 20 μm and a 0.5 M sulfuric acid solution (92 g) were loaded into a 450 mL Parr Instruments alloy C-276 batch reactor equipped with a variable speed mechanical stir and Teflon liner (Parr Instrument Co., Moline, Ill., USA). The reactor was pressurized with inert gas (35 bar) and heated to 423 K (1.4 K $min^{-1}$) with a 590 W electric heating mantle. The reactor was maintained at 423 K for 6 h while stirring. At the end of the reaction time the heating mantle was removed and the reactor was cooled with compressed air. A liquid sample (400 μL) was collected, syringe filtered (0.2 μm membrane), and analyzed by HPLC.

After a cycle of cellulose deconstruction, another batch of microcrystalline cellulose (8 g, 5% moisture) was added to the reaction mixture and the vessel was resealed. The same procedure as above was performed for multiple cycles. The solid remaining at the end of the reaction was separated from the solution via vacuum filtration and an elemental analysis for C, H, and S was performed (Galbraith Labs, Knoxville, Tenn., USA). The elemental analysis results indicated that the remaining solid composition was 67.32 wt % carbon, 4.83 wt % hydrogen and 0.06 wt % sulfur.

Figure 5:
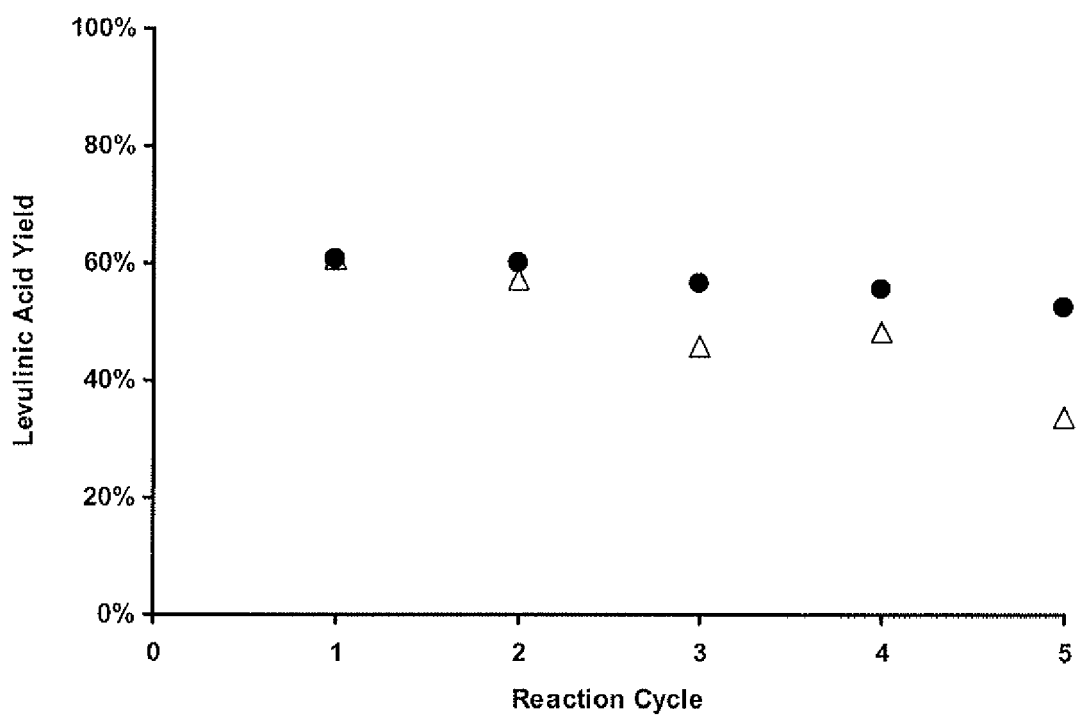
FIG. 5 is a graph depicting levulinic acid percent yield per cycle (Δ) and cumulative (●) for the deconstruction of cellulose in 0.5 M sulfuric acid at 423 K.

The results of five cellulose deconstruction cycles are shown in FIG. 5. The levulinic acid yield is above 60% for the first cycle and gradually decreased with each recycle. The final overall levulinic acid yield is about 52%. The number of moles of formic acid produced was equal to the number of moles of levulinic acid formed (within about 5%).

Example 4

Levulinic Acid Reduction to γ-Valerolactone

The levulinic acid and formic acid solution resulting from the 5-cycle cellulose deconstruction experiment discussed above was reacted over a 5 wt % Ru/C catalyst (1.02 g, Sigma Aldrich). The catalyst and a sample of the prepared solution (40 g, 15 wt % levulinic acid, 7.5 wt % formic acid) was loaded into a 450 mL Parr Instruments alloy C-276 batch reactor equipped with a variable speed mechanical stir and Teflon liner. The reactor was purged with inert gas and then pressurized with hydrogen (35 bar) at ambient temperature. The reactor was heated to 423 K (1.4 K $min^{-1}$) and then held constant for 4 h. Samples (500 μL) were collected during reaction and analyzed by HPLC.

Figure 6:
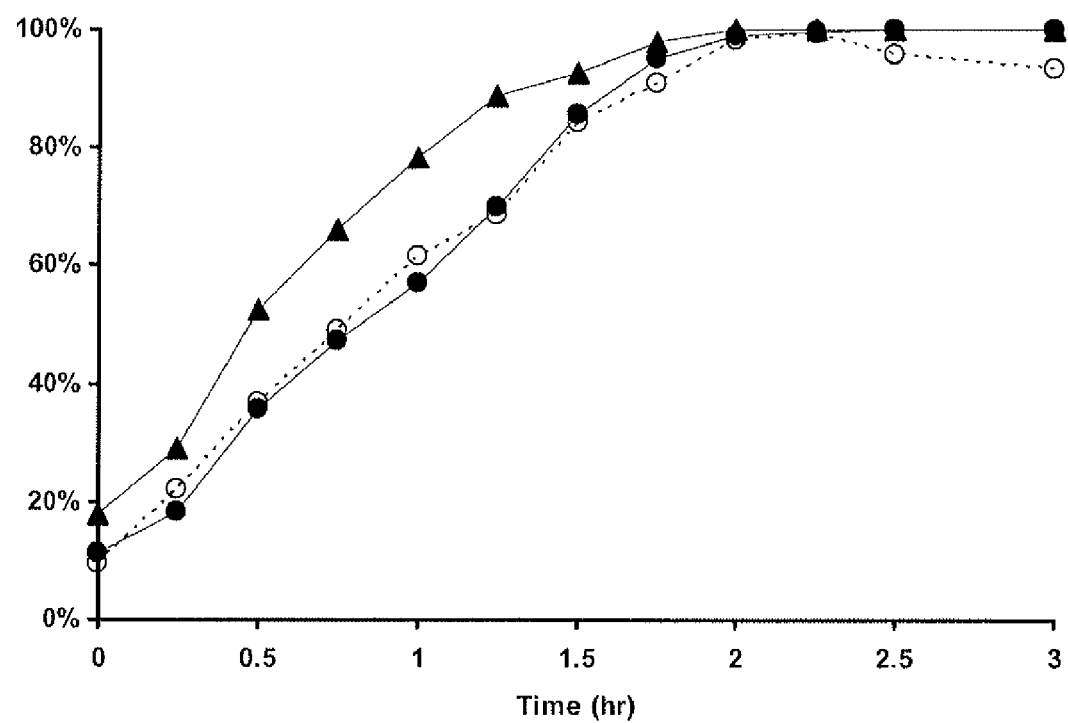
FIG. 6 is a graph depicting the conversion of levulinic acid (●), formic acid (▲), and GVL percent yield (○) over 5 wt % Ru/C at 423 K.

Detailed results of the degradation of formic acid to $CO_2$ and $H_2$ and the reduction of levulinic acid to GVL are shown in FIG. 6. The rates of conversion of formic acid and levulinic acid are similar for the reaction conditions tested. Essentially a quantitative yield of GVL was observed at approximately 2 h reaction time at 423 K. Degradation of GVL was observed at reaction times greater than the time required to completely convert levulinic acid to GVL (e.g., about 10% degradation in 10 h). The pH of the solution remained constant during levulinic acid reduction.

Example 5

γ-Valerolactone Extraction with Ethyl Acetate

Ethyl acetate (96%, Sigma Aldrich) was used to extract GVL from the solution prepared by the deoxygenation of levulinic acid discussed above. A sample (5.001 g, 1.068 g/mL) of the GVL solution was mixed with ethyl acetate (4.996 g) in a sealed glass container and shaken vigorously for 1 min. The solution was allowed to settle and the ethyl acetate layer was removed with a transfer pipette (5.309 g). The remaining aqueous layer (4.736 g, 1.062 g/mL) was analyzed by HPLC. It was determined that 76% of the GVL was extracted into the ethyl acetate as well as 3% of the $H_2SO_4$ and 6% of the water.

Extraction experiments were performed for solutions of varying concentrations of GVL (5, 20, 35, 50 wt %) and sulfuric acid (0.2, 0.5, 1.0 M). Equal masses of aqueous solution and ethyl acetate were used for the extraction following the same procedure described above. The results for the extractions are shown in Table 2. The percent extraction for compound i is calculated as the moles of i transferred to the ethyl acetate layer divided by the moles of i initially in the aqueous layer prior to ethyl acetate addition. It was observed that the percent of GVL extracted into the ethyl acetate layer increases with increasing GVL loading. The amount of water extracted into the ethyl acetate layer increased with increasing GVL extraction, while the sulfuric acid extraction increased only for the highest GVL concentration tested. The effect of sulfuric acid concentration on the extraction of GVL and water was minimal for a 20 wt % GVL solution.

Example 6

Evaporative Separation of GVL from Sulfuric Acid

The evaporative separation of GVL from sulfuric acid was modeled in Matlab software (The Mathworks, Natick, Mass., USA) by solving vapor-liquid equilibrium relations and also using AspenTech chemical simulation software (Aspen Technology, Inc., Burlington, Mass., USA). A 20 wt % GVL solution containing 0.1 M sulfuric acid was used as the feed into a separation unit. A flash drum operating at a specified temperature and pressure was modeled for both simulation methods. Each model assumed that the solution entered the flash drum at the temperature and pressure of the flash drum. For all calculations, the operating pressure was set at a desired value and held constant while the temperature required to vaporize 79% of the GVL was determined. Hydrogen, as an inert sweep gas, was introduced to determine the effect of sparging.

For Matlab simulations, the vapor-liquid equilibrium equations for GVL, water and sulfuric acid were derived assuming ideal mixing in the gas and liquid phase. The ideal gas law was used as the equation of state. Temperature dependent vapor pressures were calculated using the Antoine equation with tabulated values for the appropriate constants. The resulting series of vapor-liquid equilibrium equations were solved using the Matlab function 'fsolve'. A series of simulations at varying system pressure were performed for a hydrogen-to-GVL molar ratio of 2:1.

TABLE 2

Ethyl acetate extraction of γ-valerolactone in the presence of sulfuric acid.

| | 5 wt % GVL | 20 wt % GVL | | | 35 wt % GVL | | 50 wt % GVL | |
|---|---|---|---|---|---|---|---|---|
| | 0.2 M H2SO4 | No Acid | 0.2 M H2SO4 | 0.5 M H2SO4 | 1 M H2SO4 | 0.5 M H2SO4 | 1 M H2SO4 | 0.5 M H2SO4 | 1 M H2SO4 |
| GVL Extraction | 73% | 75% | 76% | 75% | 76% | 82% | 82% | 87% | 86% |
| H2SO4 Extraction | 2% | — | 3% | 4% | 3% | 2% | 3% | 12% | 15% |
| Water Extraction | 5% | 5% | 6% | 4% | 8% | 12% | 13% | 18% | 17% |

TABLE 3

Reaction kinetics results for the conversion of GVL to pentanoic acid in the presence of sulfuric acid.

| | | | | GVL | C distribution (%) | | | | $C_9$=O | | C selectivity (%) | | |
|---|---|---|---|---|---|---|---|---|---|---|---|---|---|
| Entry | Catalyst | Feed | T (K)/P (bar)/ WHSV ($h^{-1}$) | Conversion (%) | Aq | Org | Gas | PA (Ester) | (+stoich. $CO_2$) | $CO_x$ | $C_4 + C_5$ Alkanes | Pentanal/ 1-Pentanol | $C_6$-$C_7$ Ketones |
| 1 | Pd(5%)/Nb$_2$O$_5$ | 30% GVL- 0.02 M H$_2$SO$_4$ | 538/14/0.5 | 97 | — | 94 | 6 | 86 (1) | — | 1 | 9 | 3 | — |
| 2 | Pd(5%)/Nb$_2$O$_5$ | 30% GVL- 0.02 M H$_2$SO$_4$ | 538/14/0.4 | 99 | — | 93 | 7 | 85 (1) | — | 1 | 10 | 3 | — |
| 3 | Pd(5%)/Nb$_2$O$_5$ | 40% GVL- 0.04 M H$_2$SO$_4$ | 548/14/0.7 | 84 | 1 | 97 | 2 | 92 (—) | — | 1 | 5 | 2 | — |
| 4 | Pd(5%)/Nb$_2$O$_5$ | 40% GVL- 0.02 M H$_2$SO$_4$ | 548/7/0.3 | 93 | 1 | 95 | 4 | 92 (—) | — | 1 | 5 | 2 | — |
| 5 | Pd(5%)/Nb$_2$O$_5$ | 40% GVL- 0.02 M H$_2$SO$_4$ | 548/1/0.3 | 70 | 2 | 95 | 3 | 94 (—) | — | 1 | 4 | 1 | — |
| 6 | Pd(5%)/Nb$_2$O$_5$ | 40% GVL- 0.02 M H$_2$SO$_4$ | 598/1/0.3 | 99 | — | 91 | 9 | 85 (—) | 4 (5) | 2 | 7 | 2 | |
| 7 | Pd(5%)/Nb$_2$O$_5$ Ce$_{0.5}$Zr$_{0.5}$O$_2$ | 40% GVL- 0.02 M H$_2$SO$_4$ | 548/14/0.8 623/14/0.5 | 98 | — | 95 | 5 | 73 (—) | 18 (19) | 2 | 5 | 1 | 1 |
| 8 | Pd(5%)/Nb$_2$O$_5$ Ce$_{0.5}$Zr$_{0.5}$O$_2$ | 40% GVL- 0.02 M H$_2$SO$_4$ | 548/14/0.8 648/14/0.5 | 98 | 1 | 92 | 7 | 47 (—) | 40 (45) | 5 | 5 | 2 | 1 |

For the AspenTech simulation, the compound library chemical properties for GVL, water, sulfuric acid, and hydrogen were used. The non-random two liquid (NRTL) equation of state was used for the calculations. A flash drum unit operation with a specified input material flow was used in the simulation. Simulations at varying system pressure were performed for a hydrogen-to-GVL molar ratio of 2:1 and 10:1.

Figure 7:
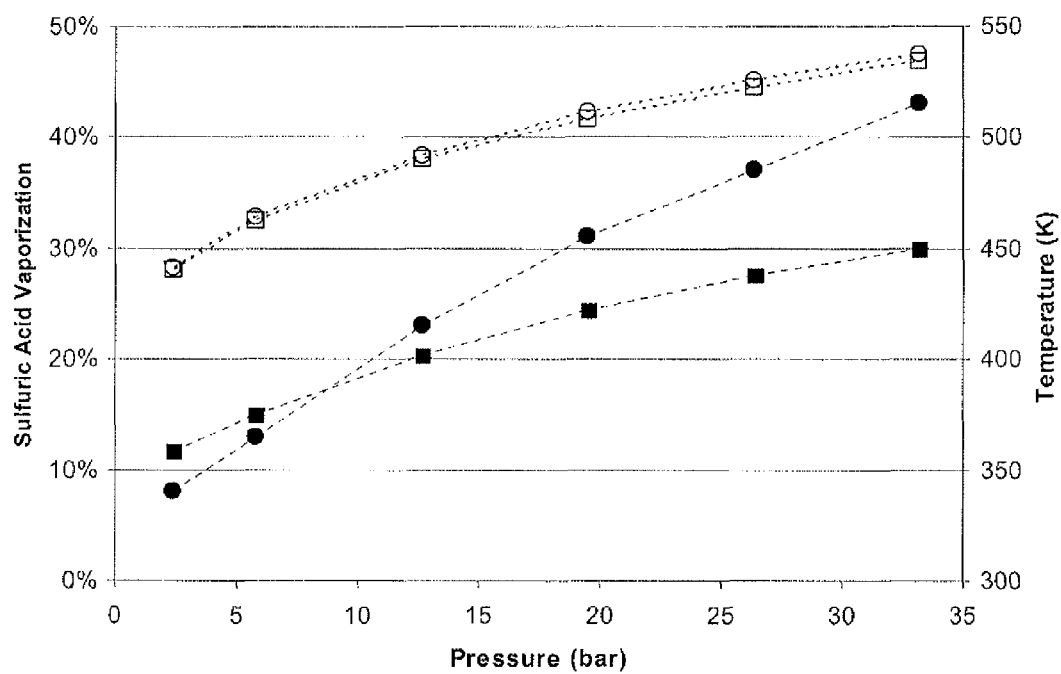
FIG. 7 is a graph depicting simulated results for vaporization of 79% GVL in sulfuric acid to determine the sulfuric acid % vaporization (■; ●) and the required vaporization temperature (□; ○) for a H$_2$ to GVL ratio of 2. Red symbols correspond to results from Matlab software, and blue symbols correspond to results using AspenTech simulation software.
Figure 8:
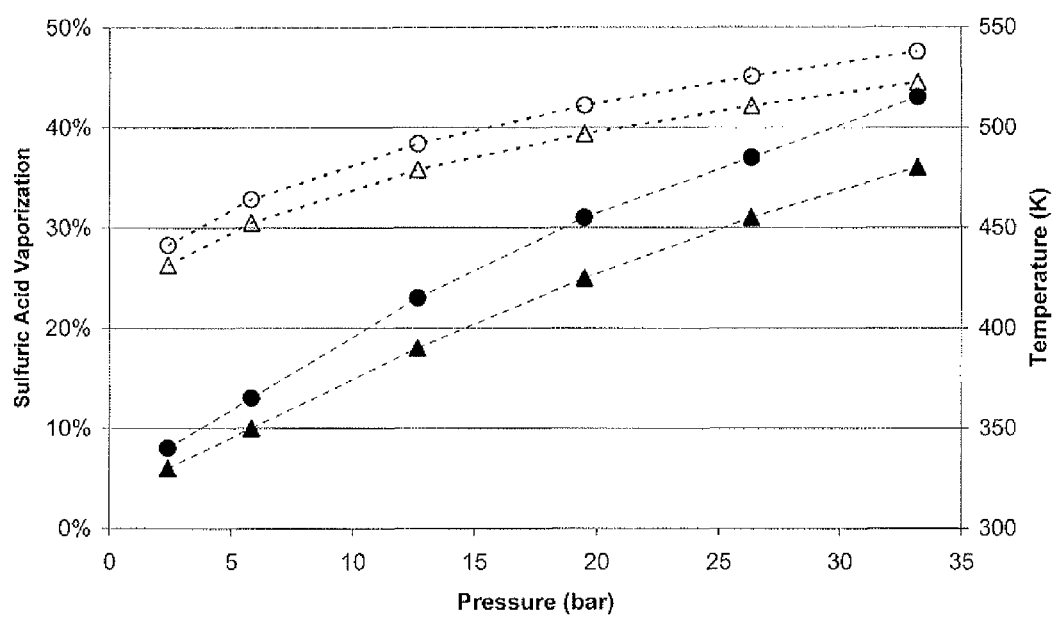
FIG. 8 is a graph depicting simulated results for the vaporization of 79% GVL in sulfuric acid using AspenTech simulation software to determine the sulfuric acid % vaporization (●) and required vaporization temperature (○) for a H$_2$-to-GVL ratio of 2:1 and also the sulfuric acid % vaporization (▲) and vaporization temperature (Δ) for a H$_2$-to-GVL ratio of 10:1.

The combined results for the Matlab and AspenTech simulations are shown in FIG. 7 and FIG. 8. There was good agreement between the Matlab and AspenTech simulations for the determined temperature required for 79% vaporization of GVL. Although the predicted sulfuric acid vaporization values were similar for the two simulation methods for low system pressures, the sulfuric acid vaporization values diverged at higher system pressures. For the AspenTech simulations at varying $H_2$-to-GVL ratios it was determined that increasing the $H_2$ flow rate decreased the temperature required to vaporize 79% of the GVL and, subsequently, less sulfuric acid was vaporized. Less than 10% of the sulfuric acid is predicted to be vaporized for system pressures below 7 bar when using a $H_2$-to-GVL ratio of 10:1.

Example 7

Figure 9:
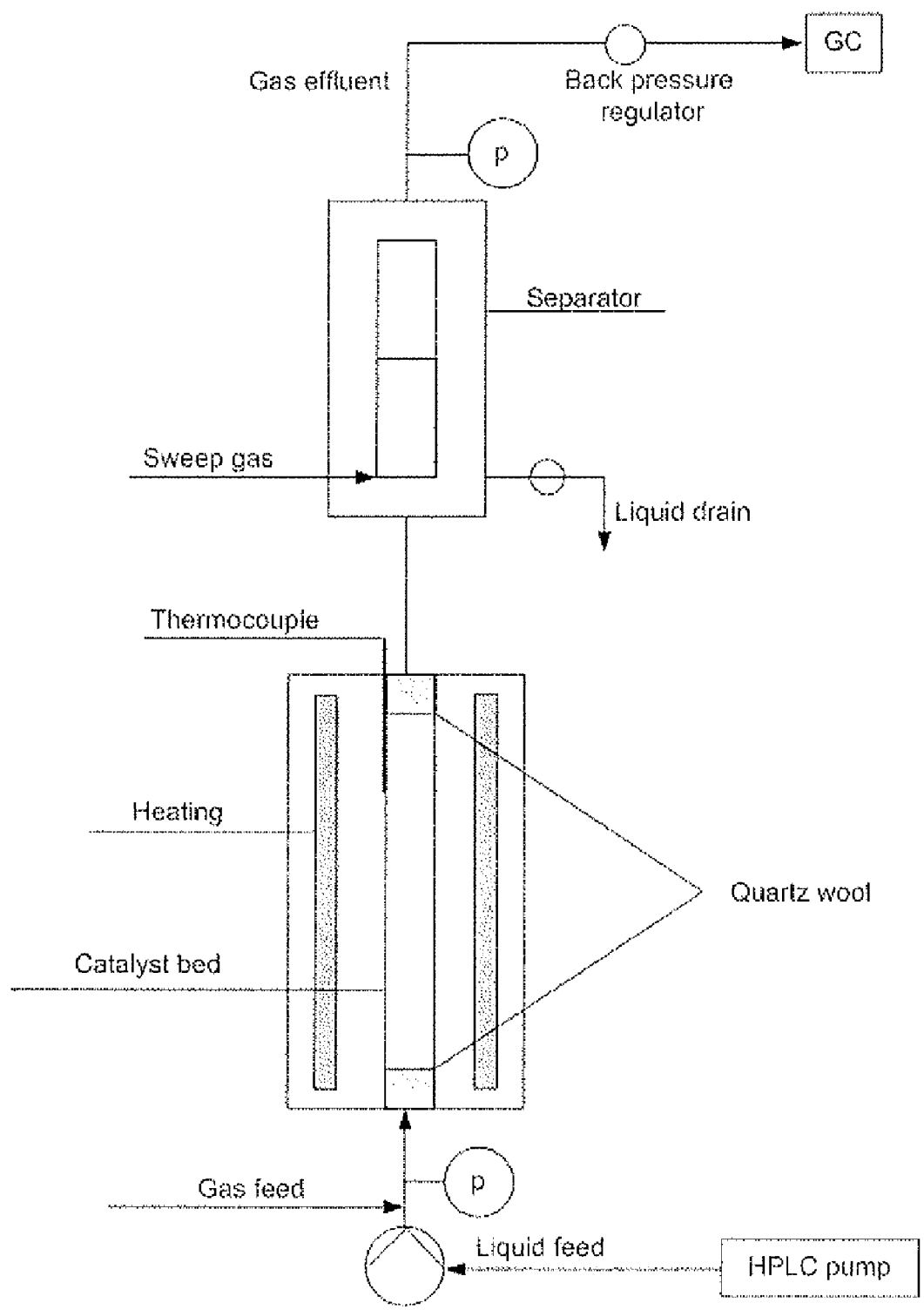
FIG. 9 is a schematic diagram of a vapor-phase flow reactor used for converting GVL to pentanoic acid as described herein.
Figure 10:
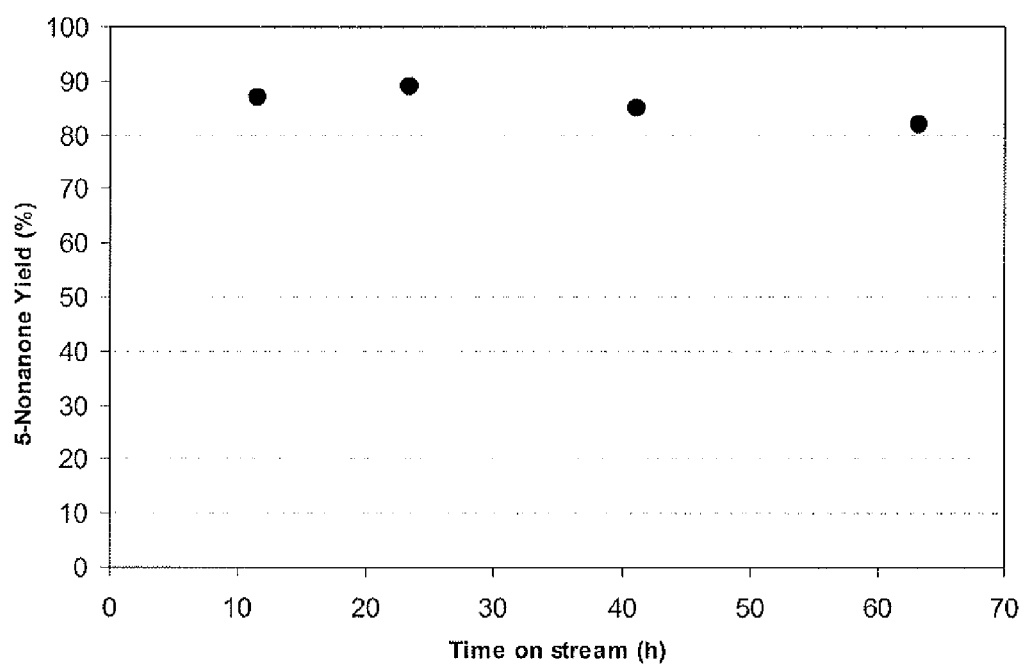
FIG. 10 is a graph depicting 5-nonanone carbon yield (% C) versus time-on-stream for the Pd(5%)/Nb$_2$O$_5$+ Ce$_{0.5}$Zr$_{0.5}$O$_2$ double-bed arrangement at 598 K-698 K, 14 bar, WHSV=0.8 h$^{-1}$–0.5 h$^{-1}$, feed: 40 wt % GVL in water and 0.02 M H$_2$SO$_4$.

Reaction Kinetics Studies for Conversion of γ-Valerolactone to Pentanoic Acid, Pentenoic Acid and n-Butenes Experimental: Pentanoic Acid Production A schematic diagram of the flow reaction system used for the reaction kinetics studies is shown in FIG. 9. A ¼" tubular reactor made of corrosion resistant commercial hastelloy C-276 alloy was used for these studies of feed solutions containing $H_2SO_4$. The catalyst (3.5 g of Pd(5%)/$Nb_2O_5$) was fixed in the tubular reactor between two end-plugs of carbon wool. For the double-bed experiments, a ¼" tubular stainless steel reactor was loaded first with Pd(5%)/$Nb_2O_5$ (3.0 g), followed by ceria-zirconia (5.0 g). Both beds were separated by a carbon wool plug. The reactor was mounted in an upflow configuration and surrounded by aluminum blocks heated externally by a well-insulated furnace (Applied Test Systems Inc.). A K-type thermocouple (Omega) was attached to the outside of the reactor to measure temperature, which was controlled with a 1600 series type temperature controller (Dwyer Instruments, Michigan City, Ind., USA). Prior to reaction kinetics studies, fresh catalyst was reduced in flowing $H_2$ (100 $cm^3$(STP) $min^{-1}$). The catalyst was heated, using a linear temperature ramp (1 K $min^{-1}$) to the final reduction temperature (538 K) and held at this temperature for 3 h, and then heated to the reaction temperature under flowing $H_2$. The flow-rate of $H_2$ was fixed with a Brooks Model 5850 mass-flow controller (Brooks Instrument, Hatfield, Pa., USA). The system pressure was controlled by a backpressure regulator (GO Regulator, Model BP-60) (GO Regulator, Spartanburg, S.C., USA). A liquid solution containing varying amounts (30-40 wt %) of GVL (Sigma-Aldrich) and sulfuric acid (0.02-0.04 M) in deionized water was introduced into the upflow reactor using an HPLC pump (Lab Alliance Series 1) (Lab Alliance, State College, Pa., USA) along with a $H_2$ co-feed flow of 30 $cm^3$(STP) $min^{-1}$. The effluent liquids (organic and aqueous) were collected at room temperature in a gas-liquid separator and drained for GC analysis. Detailed results for the GVL conversion to pentanoic acid kinetic study are shown in Tables 1 and 3. FIG. 10 shows a plot of the yield of 5-nonanone versus time-on-stream for the conversion of GVL over a double-bed consisting of Pd(5%)/$Nb_2O_5$ followed by $Ce_{0.5}Zr_{0.5}O_2$.

Experimental: Pentenoic and n-Butene Production

Amorphous silica-alumina (MCC 25, Grace Davison (Columbia, Md., USA) with a Si/Al ratio of 4), niobic acid (HY-340, CBMM), and Pd/C (1% Sigma Aldrich) were used as received.

Experiments were carried out in an ¼" outside diameter stainless steel tubular upflow reactor loaded with 0.5 to 2 g of acid catalyst mixed with crushed quartz chips (to reduce reactor dead volume) and held in place by quartz wool (Altech). For some experiments, 0.05 to 0.1 g of Pd/C was physically mixed with quartz chips or acid catalyst and quartz chips. In addition, a small preheating zone consisting of only crushed silica was placed at the inlet of the heated flow reactor. This zone was used to ensure all liquid species were vaporized prior to contacting the catalyst.

In a typical experiment, the catalysts were heated to the desired temperature under flowing hydrogen. Liquid flow was then started. The feed for all runs consisted of a 10 wt % GVL solution in water. A continuous hydrogen sweep was also used for all experiments and adjusted along with the inlet flow such that the concentration of all species into the reactor was constant for all temperatures and all values of WHSV.

Insulated aluminum blocks were heated using a K-type thermocouple ("DiGi-Sense"-brand, Eutech Instruments Pte Ltd., Singapore) between the blocks and reactors to monitor the temperature, which was controlled by a series 16A temperature controller (Love Controls, a division of Dwyer Instruments, Inc., Michigan City, Ind., USA). The $H_2$ flow rate was controlled with a 5850E Brooks Instruments mass flow controller while the liquid feed was controlled with a Lab Alliance Series 1 HPLC pump. The liquid effluents were drained from the separator and analyzed by GC (Shimadzu GC-2010, FID, SHRX5 column) and by GC-MS (Shimadzu GC-2010 SHRX1-5MS column). Gas effluents were analyzed with a Carle GC (Series 400 AGC, TCD, Porapak Q column) for CO, $CO_2$ and a Varian GC (Saturn 3, FID, GS-Q column (J&W Scientific)) for gaseous hydrocarbons. Typical total material balances closed within 10%. Molar balances closed within 20% provided no organic phase was formed. When an organic phase did form, it was collected if possible and quantified. When collection was not possible, the molar ratio of reactant and product were assumed to be the same as the aqueous layer, an assumption that underestimates the rate of production pentenoic and pentanoic acids as the organic layer is enriched in the product.

BET adsorption isotherms were used to determine catalyst surface areas while acid site density was determined by ammonia temperature programmed desorption (TPD).

Results: Pentenoic Acid and n-Butene Production

The thermodynamics of the ring opening of GVL to pentenoic acid isomers (PEA) followed by subsequent hydrogenation or decarboxylation were studied in an upflow reactor at atmospheric pressure and temperatures from 498 K to 623 K. The reactive scheme is shown in Scheme 1. First, GVL is reacted via acid-catalyzed ring opening to form 4,3-cis and 3-trans pentenoic acid. These species can further isomerize on acid sites to form 2-cis and 2-trans pentenoic acid or can revert back to GVL. The isomers of PEA can react in the absence of metal catalyst to form either butene and $CO_2$. In the presence of a metal catalyst, the PEA isomers rapidly form pentanoic acid (PAA). These studies were performed to gain insight into the production of PAA from GVL.

Scheme 1. Reactive pathways in the ring opening of GVL.

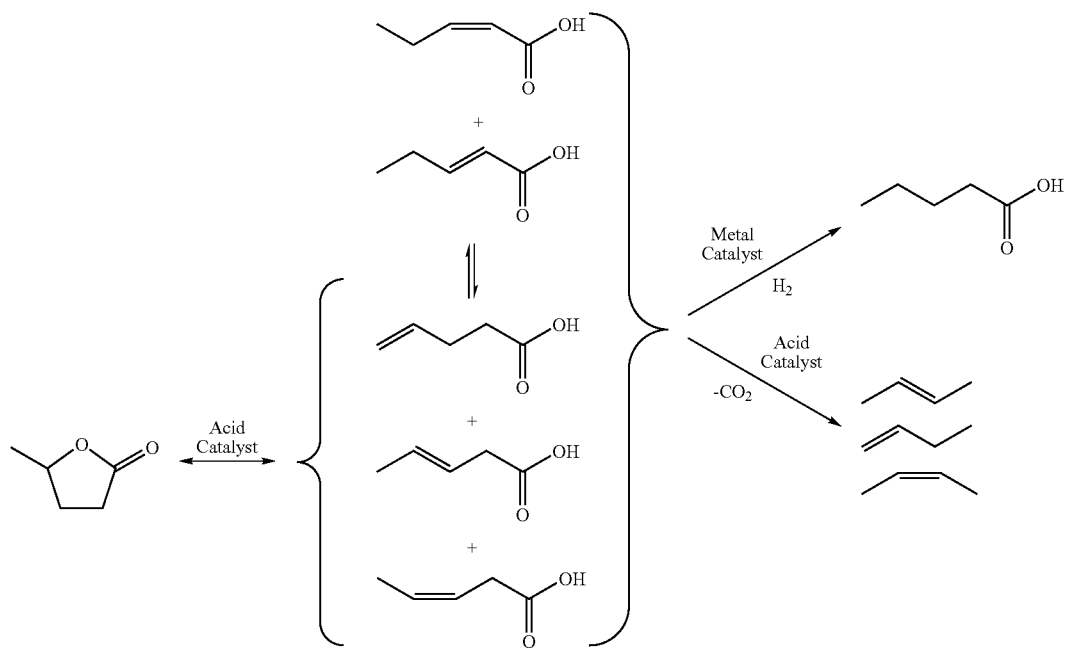

For the initial studies, silica alumina (SiAl), a relatively strong but amorphous solid acid with water tolerability was chosen. The feed for all runs comprised a 10 wt % GVL solution in water. The weight hourly space velocity (WHSV), defined as the mass of GVL per mass of catalyst per hour, was adjusted by changing either the inlet flow of feed solution, or by changing the mass of solid acid catalyst. A continuous hydrogen sweep was adjusted to keep the partial pressure of all species in the reactor constant for all temperatures and all values of WHSV at 0.016, 0.164, and 0.820 (bar) for GVL, $H_2$ and water, respectively. The hydrogen flow was chosen such that the molar ratio of $H_2$-to-GVL of 10:1.

Figure 11:
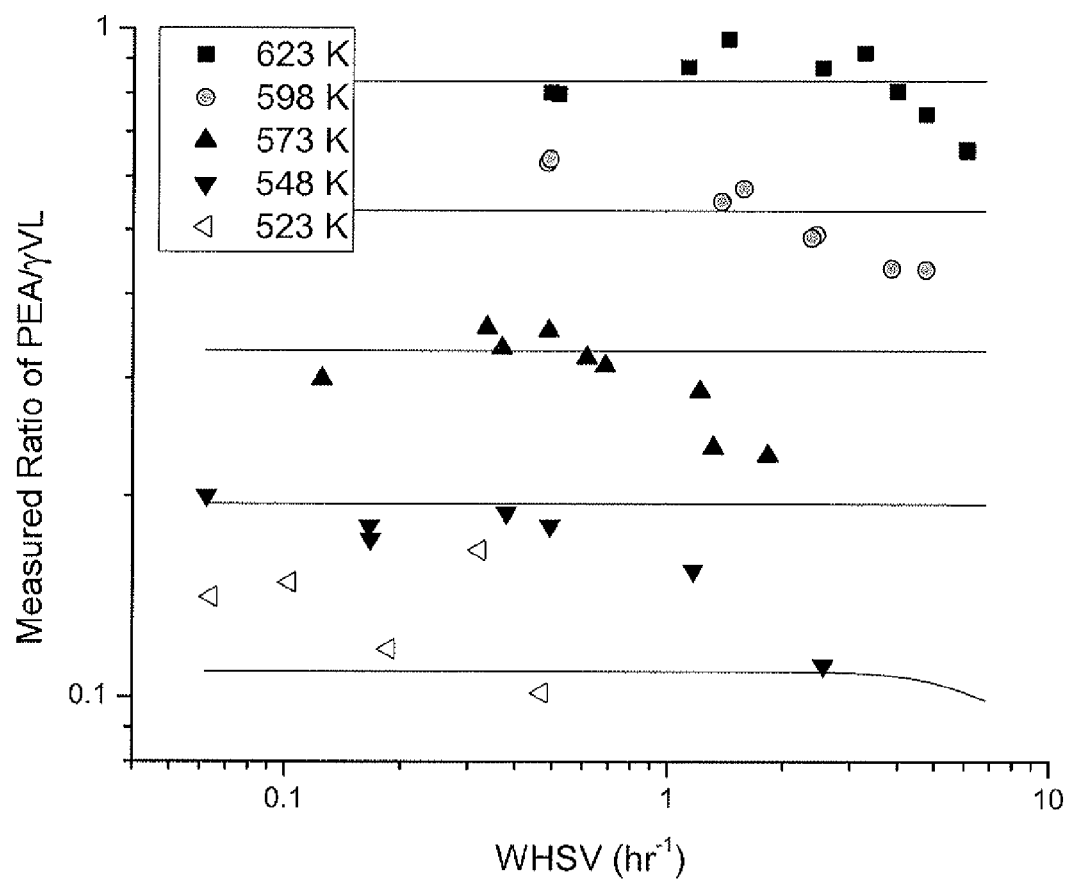
FIG. 11 is a graph depicting the ratio of outlet pentenoic acid (PEA) to GVL at increasing WHSV on SiAl. Solid lines present model fit as described in the Examples.
Figure 12:
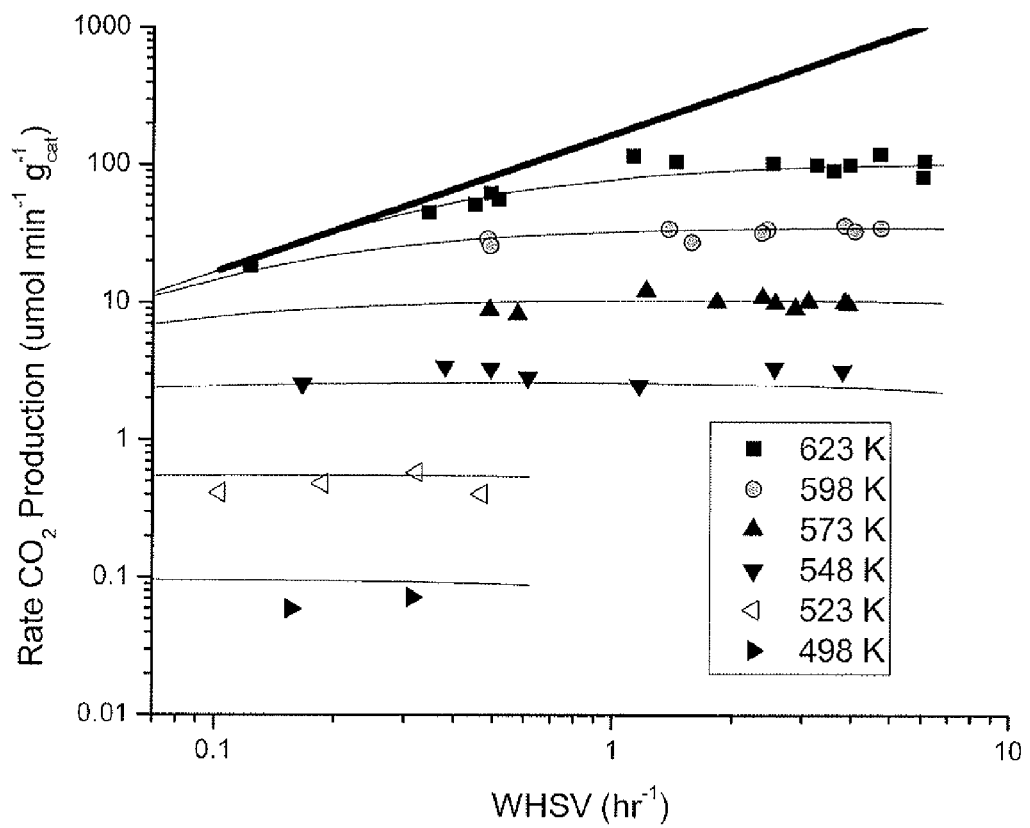
FIG. 12 is a graph depicting the rate of production of CO$_2$ at increasing WHSV on SiAl. The thick solid line corresponds to the inlet flow of GVL (μmol min$^{-1}$ g$_{cat}^{-1}$). Solid lines present model fit as described in the Examples.

The relative outlet concentration of PEA-to-GVL at temperatures of 523 to 623 K and varying WHSV are shown in FIG. 11. As the temperature increased, the ratio also increased, from an average value of 0.13 at 523 K to 0.88 at 623 K. Not included in FIG. 11 are the data points collected at 498 K and those at 623 K and low space velocity. At 498 K the low concentration of PEA was near the limit of detection for quantification. At low WHSV and 623 K, the rate of decarboxylation was greater than 80% making these points unrepresentative of the actual ratio. FIG. 12 shows the observed production of $CO_2$ over the same temperatures and WHSV values as in FIG. 11. At 498 K the average rate of $CO_2$ production was 0.07 umol min$^{-1}$ $g_{cat}^{-1}$ while at 623 K and high WHSV where the rate was not limited by the inlet flow rate of species, the rate of $CO_2$ production was 95 umol min$^{-1}$ $g_{cat}^{-1}$.

At a temperature of 623 K and a space velocity of about 0.1 to 1 h$^{-1}$ (g GVL $g_{cat}^{-1}$ h$^{-1}$), 85-100% yield of $CO_2$ and butene was observed. As a follow up to this observation, a concentrated feed solution corresponding to a typical effluent from FIG. 2A was investigated. Two feed solutions containing 30 wt % GVL solution either with or without 0.04 M $H_2SO_4$ were reacted at a temperature of 623 K and atmospheric pressure. The results are shown in Table 4.

TABLE 4

Production of Butene and $CO_2$ from GVL over Silica Alumina

|  | No $H_2SO_4$ | 0.04 M $H_2SO_4$ |
|---|---|---|
| GVL | 30 wt % | 30 wt % |
| WHSV | 0.73 hr$^{-1}$ | 0.55 hr$^{-1}$ |
| Conversion | 97.1% | 96.5% |
| Yield | 84.3% | 83.1% |
| Feed pH | 3.7 | 1.1 |
| Effluent pH | 3.2 | 1.3 |
| Time on Stream | 22.5 h | 17.5 h |

The conversion in Table 4 was calculated from the unreacted GVL observed in the liquid effluent. The yield to mixed butene isomers was calculated from the observed gas phase effluents. In addition to butene, small amounts of the products methane, ethane, ethene, propane, propene, and pentane, were observed in the gas phase. The results in Table 4 were performed over the same catalytic bed. The run without sulfuric acid was performed first, followed by the sulfuric acid run. Neither system showed deactivation with time on stream (22.5 for the first run, and 17.5 h (40 h total) for the second run) with the yield calculated by averaging 15-20 gaseous samples taken at regular intervals with time on stream.

The pH of the feed solution containing sulfuric acid should be $-\log_{10}(0.04 \times 2) = 1.1$ the same as the measured value. The effluent pH was measured at 1.3, which corresponds to a concentration of 0.025 M. The balance on sulfuric acid is therefore approximately 63%. However, the transient from the feed with no sulfuric acid through the feed with sulfuric acid was included in the sulfuric acid drain. The reactor dead volume is typically between 5 and 10 mL. Taking this into account, the sulfur balance improves to 74 and 90%.

Thus near quantitative yields of butene are possible from aqueous solutions of GVL from 10-30 wt %, both with and without low concentrations of sulfuric acid. The majority of the sulfuric acid is recovered (based on observed pH of solution).

The overall chemistry for the production of butene from a six-carbon sugar is shown in Scheme 2. In the formation of LA from sugar, formic acid and water are produced, (Scheme 2A). Formic acid can be reformed to hydrogen and subsequently used to hydrogenate levulinic acid followed by dehydration to produce GVL and a second water molecule (Scheme 2B). GVL can be decarboxylated to form butene isomers and a second carbon dioxide (Scheme 2C).

Scheme 2. Overall Balance of Sugar to Levulinic and Formic Acid (A), Sugar to GVL (B), and Sugar to Butene (C).

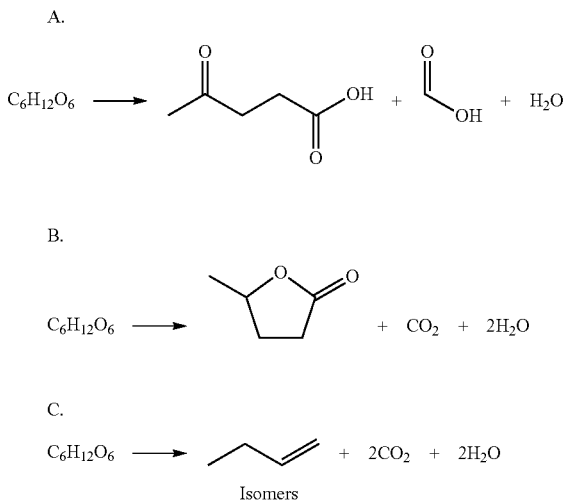

This reactive scheme as a means of producing butene from biomass is novel and inventive. The expected low cost of levulinic acid, and associated low cost of catalyst makes this process an economical way of producing a highly reactive and useful compound from biomass without supplying hydrogen to the reaction.

Figure 13:
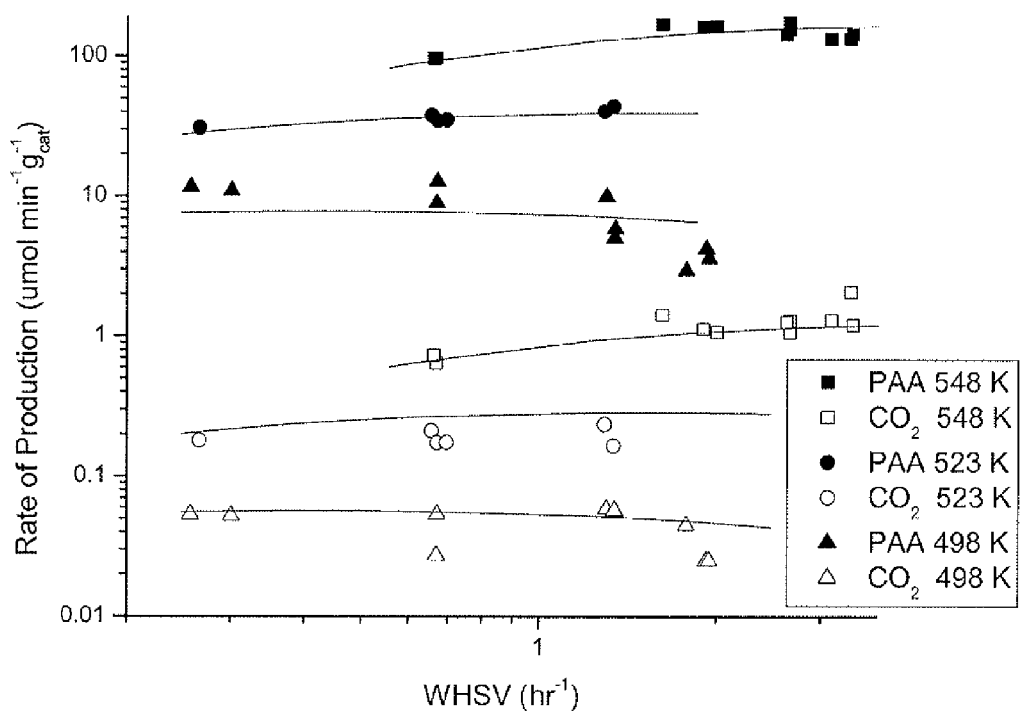
FIG. 13 is a graph depicting the rate of production of PAA and CO$_2$ over a physical mixture of 10-to-1 SiAl to Pd/C in excess H$_2$. Solid lines present model fit as described in the Examples.

In a third set of experiments, the SiAl catalyst and crushed silica were physically mixed with a 1 wt % Pd/C catalyst, with the mass of SiAl divided by the mass of Pd/C equal to 10. All other conditions were identical to experiments without Pd/C. The addition of the metal catalyst (combined with the 10-to-1 molar excess of $H_2$) allowed for the rapid hydrogenation of PEA to PAA. No PEA was detected in the effluent. The rates of production of PAA and $CO_2$ as a function of WHSV are shown in FIG. 13.

The acid-catalyzed decarboxylation of PAA to form $CO_2$ and butane was briefly studied at 673 K using a saturated solution of PAA in water ($\approx$4.9 wt %) at a WHSV of 0.18 hr$^{-1}$ and corresponding $H_2$ flow. The rate of production was found to be 0.4 µmol min$^{-1}$ g$_{cat}^{-1}$. By comparison, the calculated steady state value for PEA acid-catalyzed decarboxylation at the same temperature is greater than 900 µmol min$^{-1}$ g$_{cat}^{-1}$. Because this difference is three orders of magnitude larger for PEA, the direct acid-catalyzed decarboxylation of pentanoic acid to form butane and $CO_2$ is not an important consideration.

The Pd-catalyzed decarboxylation of pentanoic acid was also briefly studied using a saturated PAA solution in water using Pd/C and crushed silica. At 548 K the maximum metal-catalyzed decarboxylation, using a saturated PAA solution and only a metal catalyst such that no co-adsorption of alkenes or hydrogenation is occurring, was 3 µmol min$^{-1}$ g$_{cat}^{-1}$ (per metal catalyst basis). In FIG. 13, with the addition of Pd/C to the acid system, it is noted that the rate of $CO_2$ (and butane) production per acid catalyst at 548 K is approximately 1 umol/min/g$_{cat}$ (approximately 10 µmol min$^{-1}$ g$_{cat}^{-1}$ on a Pd/C basis). Therefore, with PEA and acid catalyst present, the rate of decarboxylation is over three times greater than saturated PAA solution on the metal alone. From FIG. 12, in the absence of Pd/C, pentenoic acid decarboxylates on the acid sites at a rate 2.5 times higher than when Pd/C is loaded. Therefore, it is believed that the production of $CO_2$ is due primarily to the acid-catalyzed decarboxylation of PEA and to a smaller extent, the metal-catalyzed decarboxylation of PAA.

The rate of ring opening was also measured in the absence of solid acid as a function of temperature on a system loaded with 0.1 g of Pd/C and crushed silica and operating at a flow rate of 0.04 mL min$^{-1}$. This flow rate corresponds to a typical WHSV (as defined for the solid acid catalyst) of 0.1-0.5 hr$^{-1}$. The rate of ring opening and rate of decarboxylation were approximately 3% of the comparable acid-catalyzed rates at 523 K and dropped off to less than 0.2% at 623 K, thus indicating that crushed silica and Pd/C do not contribute significantly to the ring opening of GVL.

Figure 14:
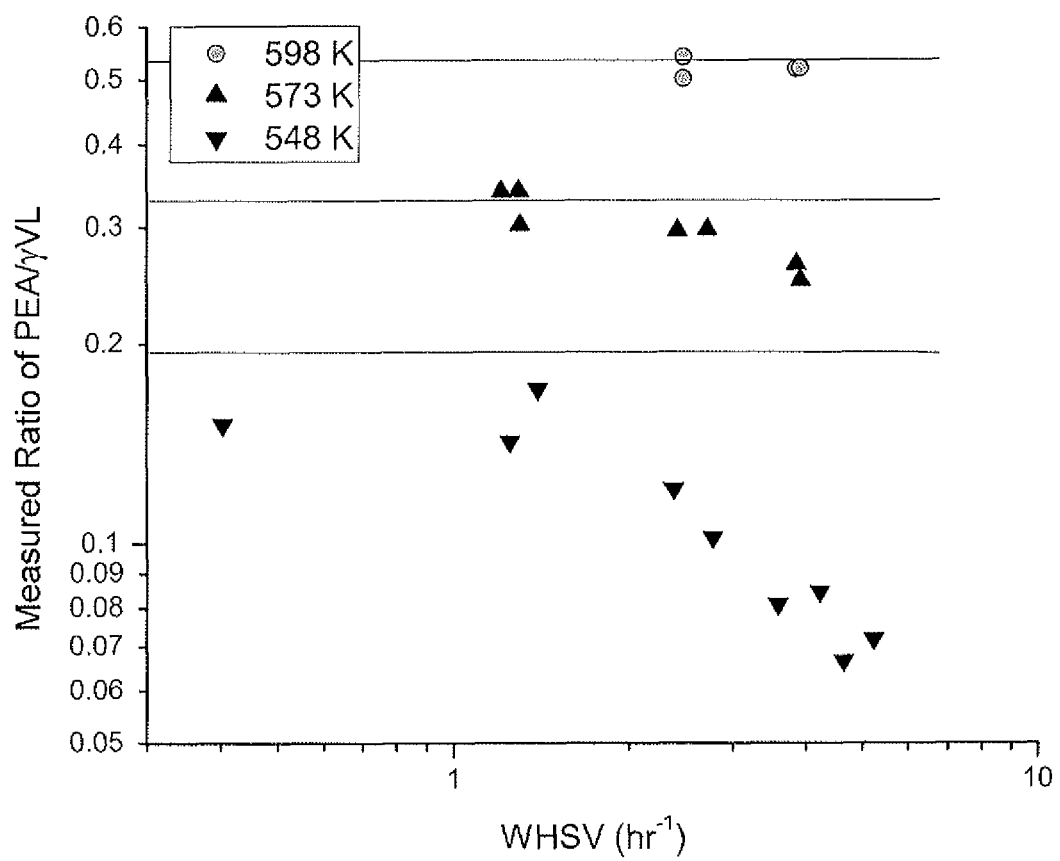
FIG. 14 is a graph depicting the ratio of outlet PEA to GVL at increasing WHSV on Nb. Solid lines present model fit as described in the Examples.
Figure 15:
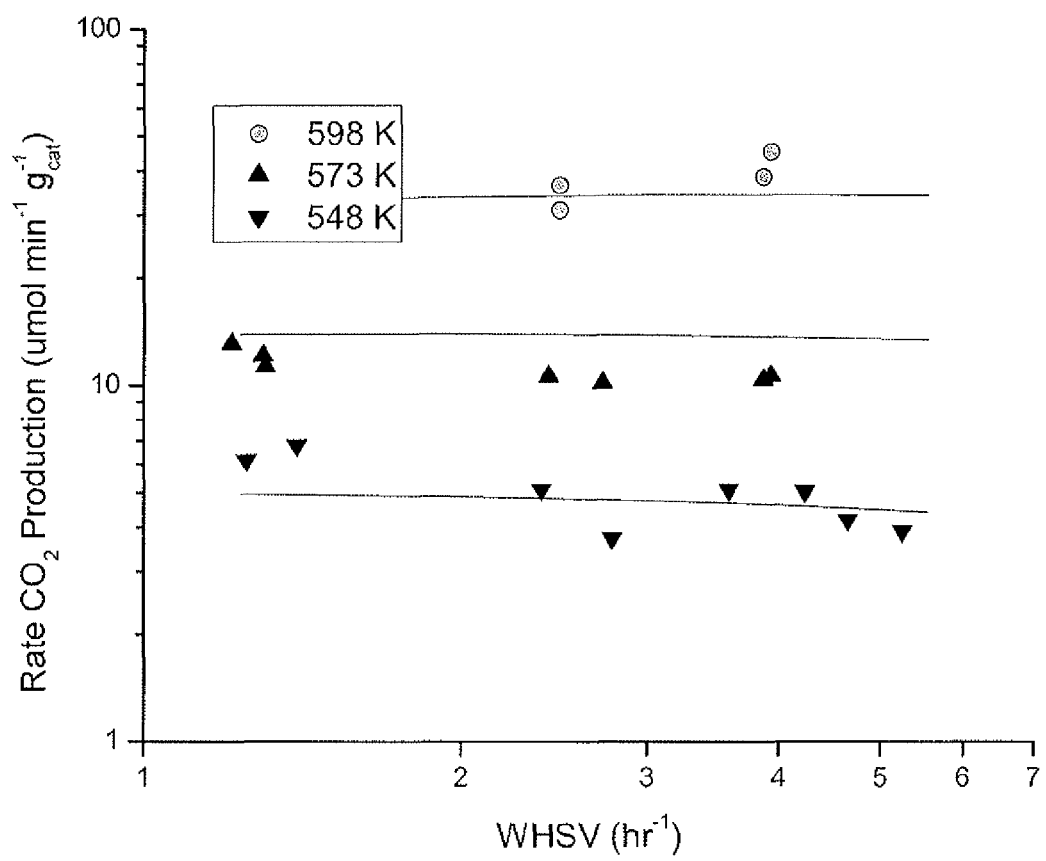
FIG. 15 is a graph depicting the rate of production of CO$_2$ at increasing WHSV on Nb. Solid lines present model fit as described in the Examples.

The activity of a second catalyst, niobic acid (Nb) was investigated under identical conditions as SiAl. FIG. 14 shows the relative outlet concentration of PEA to GVL at temperatures of 548 to 598 K and varying WHSV. As with SiAl, an increase in temperature increases the ratio of PEA to GVL from an average value of 0.16 at 548 K to 0.52 at 598 K. The observed production of $CO_2$ over the same temperatures and WHSV values as FIG. 14 is shown in FIG. 15. The average rate of $CO_2$ production spans from 0.48 to 38 µmol min$^{-1}$ g$_{cat}^{-1}$ from 548 to 598 K.

Figure 16:
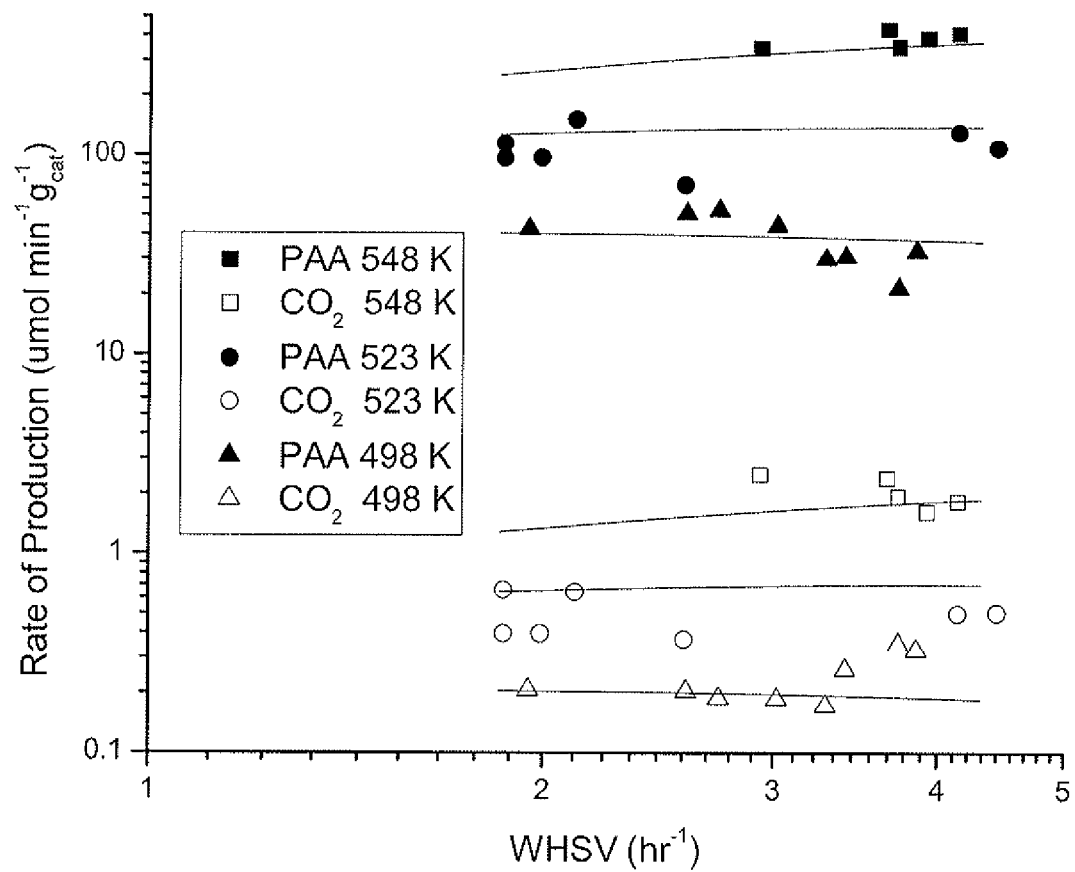
FIG. 16 is a graph depicting the rate of production of PAA and CO$_2$ over physical mixture of 7 to 1 Nb to Pd/C in excess H$_2$. Solid lines present model fit as described in the Examples.

In a final set of experiments, the Nb solid acid, crushed silica and 1 wt % Pd/C were physically mixed with a ratio of solid acid-to-metal catalyst equal to 7. All other conditions were identical to experiments without Pd/C. As with SiAl, the hydrogenation of PEA to PAA was rapid such that no PEA was detected in the outlet. The rates of production of PAA and $CO_2$ as a function of WHSV are shown in FIG. 16.

Discussion:

The modeled reactive pathway is shown in Scheme 3. (Applicants provide the proposed mechanism for discussion only and are not limited to any specific mechanistic pathway from GVL to pentanoic acid.) First GVL is reacted via acid-catalyzed ring opening to form 4,3-cis and 3-trans pentenoic acid which can revert back to GVL. These species were found to rapidly isomerize on acid sites to form 2-cis and 2-trans pentenoic acid. The production of these species as the ring opening products is supported by recent work in which the ring of GVL was opened and the acid reacted via esterification under distillation conditions to produce the methyl esters. The 4-position ester was formed in 25-30% yield, while the 3-cis and 3-trans were formed in 65-75% yield with the 2-cis and 2-trans making up the remaining 1-5%. In this system, the directly formed isomers are removed before isomerization, while in the current investigation, they are not and can thus isomerize to the 2-cis and 2-trans isomers. The isomers of PEA can react in the absence of metal catalyst to form butene and $CO_2$. However, in the presence of a metal catalyst the isomers rapidly form PAA.

Scheme 3. Reactive pathway model

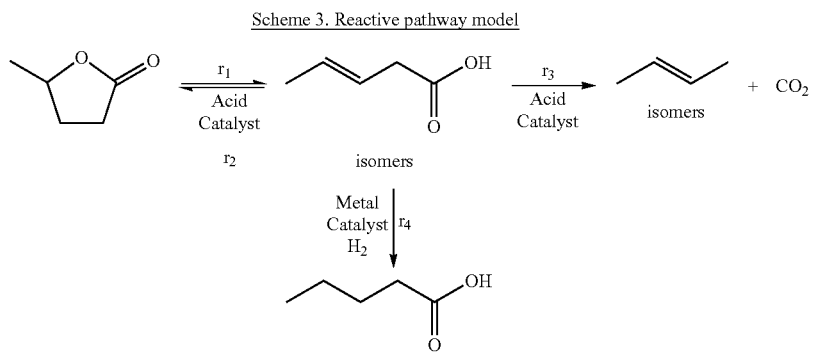

Figure 17:
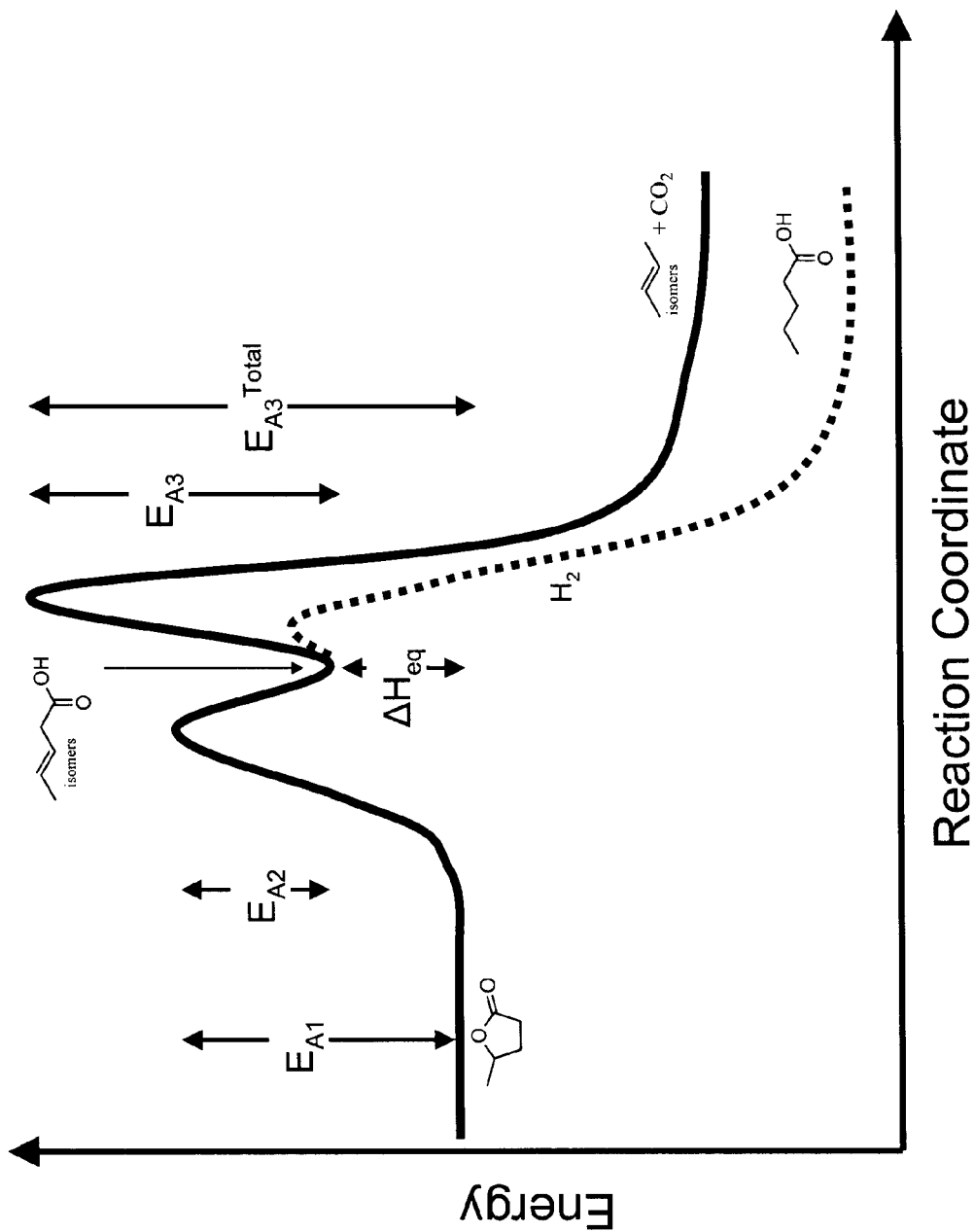
FIG. 17 is an energy diagram for producing of PAA, butene, CO$_2$ and PEA from GVL.

The total energy diagram for this system can be represented as shown in FIG. 17. In the absence of metal catalyst, the system follows the solid line. When a metal catalyst and hydrogen are present, the system follows the dashed line. Prior to experiments, the molecules involved in this study were simulated using Gaussian-brand software (Gaussian, Inc., Walingford, Conn., USA). Starting from GVL, the formation of either butene and $CO_2$ or PAA, are calculated as favored at all temperatures with standard enthalpy of −22 kJ $mol^{-1}$ and Gibbs energy change −77 kJ $mol^{-1}$ at 298 K for GVL to $CO_2$ and butene. For the conversion of GVL plus $H_2$ to PAA, values of −84 kJ $mol^{-1}$ and −59 kJ $mol^{-1}$, respectively, were used.

At standard conditions, thermodynamics favors the formation of GVL over PEA isomers. Values for the ring opening of GVL to 4-pentenoic acid were calculated as having an enthalpy of reaction of 36 kJ $mol^{-1}$ at 298 K which compares favorably with the reported literature value of 38-40 kJ $mol^{-1}$. The other isomers of pentenoic acid were calculated to have a lower enthalpy of reaction from GVL with 2-trans having the lowest value, 17 kJ $mol^{-1}$, followed by 3-trans, 2-cis, and lastly 3-cis with values of 25, 26, 32 kJ $mol^{-1}$, respectively. The calculated change in Gibbs energy at 298 K for GVL to PEA isomers follows the same trend as the enthalpy with values of 25, 8, 14, 16, and 19 kJ $mol^{-1}$ for 4,2-trans, 3-trans, 2-cis, and 3-cis. Interestingly enough, in this study the concentration of 2-trans pentenoic acid, the thermodynamically most stable isomer, was in all cases the largest while the concentration of 4-pentenoic acid, the least stable isomer, was always in lowest concentration. For the sake of simplicity, the isomerization of pentenoic acids was assumed to be equilibrated under the reactive conditions such that the total concentration of all pentenoic acid isomers was modeled instead of the individual concentrations.

Assuming equilibrium among the PEA isomers and GVL, the expected concentrations as a function of temperature can be calculated using the simulated thermodynamic values including the calculated heat capacity. Over the temperature range of this study, the simulated change in enthalpy and entropy for GVL to all PEA isomers is 25 kJ $mol^{-1}$ and 53 J $mol^{-1}$ $K^{-1}$, respectively. At approximately 473 K, the formation of PEA becomes more favorable than the formation of GVL. It is therefore expected, that as the temperature is increased, the relative ratio of PEA to GVL should also increase. When equilibrium is established, this ratio should remain constant. At higher flows, if the forward rate of ring opening is to slow relative to the inlet flow of reactant, this ratio should decrease.

From FIGS. 11 and 14, it is noted that the ratio of PEA/GVL is also approximately constant at lower space velocities but begins decreasing as the flow rate is increased. From FIGS. 12 and 15, it is apparent that the rate of carbon dioxide production is independent of WHSV. Because the production of $CO_2$ and butene is independent of feed rate, and because the ratio of PEA/GVL is constant, it can be assumed that reactions leading to the total production of PEA, namely the ring opening of GVL to and isomerization of PEA are quasi-equilibrated.

In this quasi-equilibrated state, the forward rate of ring opening, $r_1$, is balanced by the ring closing, $r_2$, and decarboxylation, $r_3$ as shown in equation 1.

$$r_1 = r_2 + r_3 \tag{1}$$

The forward rate of reaction of each species is assumed to be first order in each reactant such that the individual rates for $r_1$-$r_4$ can be written as shown in equations 2-5.

$$r_1 = k_1 P_{\gamma VL} = A_1 \exp^{\frac{-E_{a1}}{RT}} P_{\gamma VL} \tag{2}$$

$$r_2 = k_2 P_{PEA} = A_2 \exp^{\frac{-E_{a2}}{RT}} P_{PEA} \tag{3}$$

$$r_3 = k_3 P_{PEA} = A_3 \exp^{\frac{-E_{a3}}{RT}} P_{PEA} \tag{4}$$

$$r_4 = k_4 P_{PEA} \tag{5}$$

With the quasi-equilibrium established, the observed ratio $K_{obs}$ can be defined as shown in equation 6, with $r_3$, the rate of $CO_2$ production rewritten as equation 7.

$$K_{obs} = \frac{P_{PEA}}{P_{\gamma VL}} = \frac{k_1}{k_2 + k_3} \tag{6}$$

$$r_3 = k_3 K_{obs} P_{\gamma VL} \tag{7}$$
$$= A_3 \exp^{\frac{-E_{a3}}{RT}} K_{obs} P_{\gamma VL}$$
$$= k_3^{Total} P_{\gamma VL}$$
$$= A_3^{Total} \exp^{\frac{-E_{a3}^{Total}}{RT}} P_{\gamma VL}$$

The change in $r_3$ versus temperature is known from FIG. 12 for SiAl and FIG. 15 for Nb. Because no PEA was observed in the effluents when Pd/C was added to the system, it can be assumed that the rate of PAA production, $r_4$, in FIGS. 13 and 16 is equal to $r_1$, the forward rate of ring opening. Therefore, $Ea_1$ and $Ea_3^{Total}$ can be calculated for both catalysts by plotting the natural logarithm of the average rates of production versus reciprocal temperatures as shown in FIG. 18.

Figure 18:
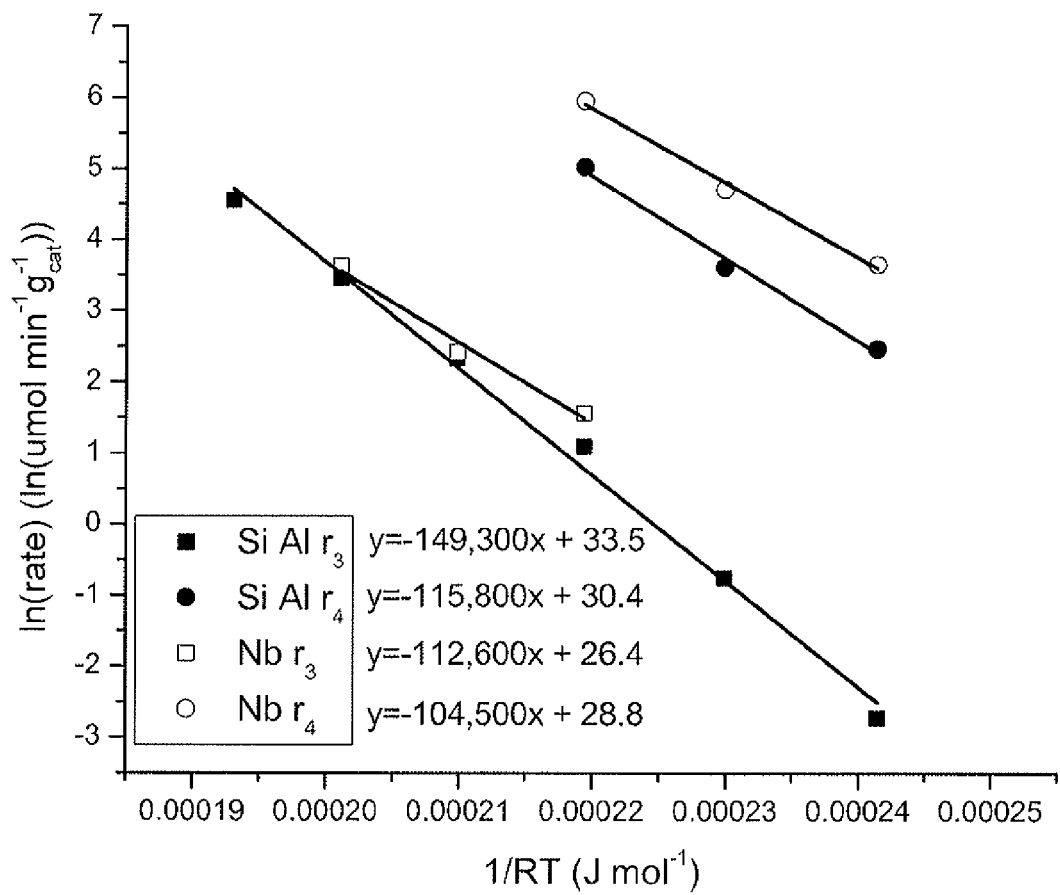
FIG. 18 is a graph depicting an Arrhenius plot for production of PAA (r$_4$) and CO$_2$ (r$_3$) on SiAl and Nb.
Figure 19:
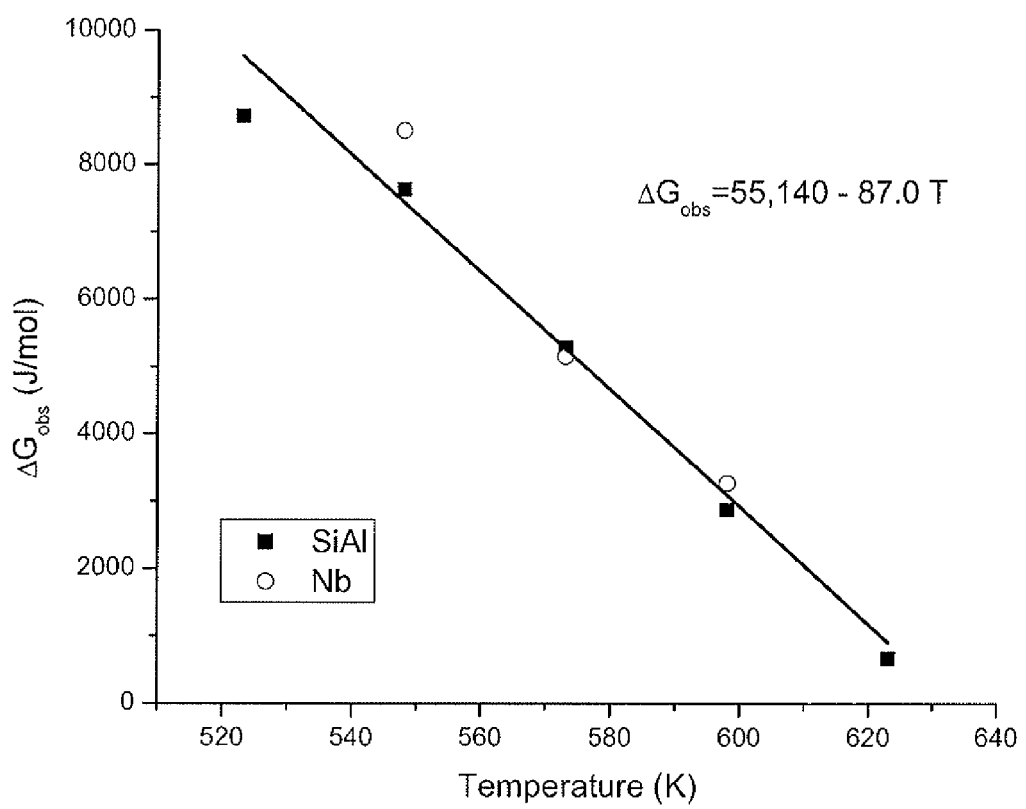
FIG. 19 is a graph depicting calculated change in ΔG$_{obs}$ versus temperature.

From FIG. 18, the activation energy for ring opening, $Ea_1$, on SiAl and Nb is 149 and 112 kJ mol$^{-1}$, respectively, while the total activation energy for $CO_2$ production is 113 and 104 kJ mol$^{-1}$, respectively. Using these relationships, the difference between $r_3$ and $r_1$ for SiAl ranges from 0.7% at 498 K to 3.8% at 623 K while Nb ranges from 1.0% to 1.5% over the same temperatures. Since $r_1 \gg r_3$, $r_2 \gg r_3$, by equation 1 the observed ratio of PEA to GVL, $K_{obs}$, can be written according to equation 8 and be taken as an approximate equilibrium value for the conditions of this study. Plotting equation 9 for the observed values versus temperature allows the extraction of observed enthalpy and entropy terms for the PEA, GVL equilibrium as shown in FIG. 19. The calculated enthalpy value, $\Delta H_{obs}$ is 55 kJ mol$^{-1}$, while the calculated entropy value, $\Delta S_{obs}$ is 87 J mol$^{-1}$ K$^{-1}$.

$$k_{obs} = \frac{P_{PEA}}{P_{\gamma VL}} \approx \frac{k_1}{k_2} \qquad (8)$$

$$-RT \ln(K_{obs}) = \Delta G_{obs} = \Delta H_{obs} - \Delta S_{obs} T \qquad (9)$$

These values are much higher than the simulated enthalpy and entropy values of 25 kJ mol$^{-1}$ and 53 J mol$^{-1}$ K$^{-1}$, respectively. At 298 K, however, a recent paper estimated $\Delta G$ of the ring opening of GVL to trans-3-pentanoic acid as 25 kJ mol$^{-1}$ (Lange, 2007). The corresponding value calculated here from the experiments (for all isomers) is 29 kJ mol$^{-1}$ while the simulated value is 9 kJ mol$^{-1}$ for all isomers and 14 kJ mol$^{-1}$ for trans-3-pentanoic acid. For the sake of studying the current system, the observed values will be assumed as accurate and used for the model fit, although the calculated values were also fit with out success.

From the extracted values presented above, $Ea_2$ and $Ea_3$ can be calculated for each catalytic system from equations 10 and 11.

$$Ea_2 = Ea_1 - \Delta H_{obs} \qquad (10)$$

$$Ea_3 = Ea_3^{Total} - \Delta H_{obs} \qquad (11)$$

For SiAl, $Ea_1$ is 113 kJ mol$^{-1}$ and $E_{a3}^{Total}$ is 149 kJ mol$^{-1}$. With an $\Delta H_{obs}$ of 55 kJ mol$^{-1}$, $Ea_2$ by difference is 58 kJ mol$^{-1}$ while $Ea_3$ is 94 kJ mol$^{-1}$. For Nb, $Ea_1$ is 104 kJ mol$^{-1}$, while $E_{a3}^{Total}$ is 113 kJ mol$^{-1}$. Therefore, $Ea_2$ is 49 kJ mol$^{-1}$ while $Ea_3$ is 58 kJ mol$^{-1}$.

A kinetic model for this system was constructed next using the parameters extracted above. The observed enthalpy and entropy values, ($\Delta H_{obs}$=55 kJ mol$^{-1}$, $\Delta S_{obs}$=−87 J mol$^{-1}$ K$^{-1}$) were not adjusted but rather were kept constant. The activation energy and pre-exponential constant for the ring opening of GVL r1, and decarboxylation of PEA to $CO_2$ and butene, $r_3$, were fit using the calculated values from FIG. 18 as the initial guesses. Initial values of the pre-exponential constant were calculated using FIG. 18 and equations 7-9 to ensure thermodynamic consistency.

The kinetic model solved from these initial guesses, the rates of reaction (equations 2-5) for each species by comparing the observed and predicted responses. The only assumption in this model was that the observed enthalpy and entropy values were correct. The initial guesses along with the final fits are given in Table 1. The final model fits can be seen on FIGS. 11-16. The parameter estimation was performed in Matlab using 'nlinfit' with the confidence intervals calculated from the residuals and Jacobian using the 'nlparci' function.

Because the value of $k_4$, the rate constant corresponding to hydrogenation of the metal sites, is unknown but assumed to be quite high, it was estimated as follows. From FIGS. 13 and 16, it is apparent that the production of PAA is accompanied by the formation of $CO_2$. As previously discussed, it is known that the direct decarboxylation of PAA on the acid portion does not significantly contribute to the formation of $CO_2$. Since the rate of decarboxylation of the metal catalyst under optimum conditions (saturated PAA solution, no other co-adsorbing species) was 30% of the observed total decarboxylation, it was assumed for simplicity that the rate of decarboxylation on the metal catalyst was also insignificant such that the only source of $CO_2$ was from the decarboxylation of PEA on the acid sites. With this assumption, the ratio of $r_4$ and $r_3$ as observed in FIGS. 13 and 16 will also be the ratio of $k_4$ to $k_3$ respectively from equations 4 and 5. For SiAl, $k_4/k_3$ is 137, for Nb it is 198. See Table 5 for details.

TABLE 5

Activation Energy and Pre-Exponential Values for Ring Opening and Decarboxylation of SiAl and Nb.

| Rate | Source | SiAl | | Nb | |
| --- | --- | --- | --- | --- | --- |
| | | Ea[a] | lnA[b] | Ea | lnA |
| r4 (r1) | FIG. 17 | 116 | 35 | 105 | 33 |
| r1 | Matlab | 133 ± 10 | 40 ± 2 | 112 ± 25 | 36 ± 6 |
| r3 | FIG. 17 | 94 | 27 | 57 | 20 |
| r3 | Matlab | 101 ± 6 | 29 ± 1 | 64 ± 14 | 22 ± 3 |

[a] Ea (kJ mol$^{-1}$)
[b] A (μmol min$^{-1}$ $g_{cat}^{-1}$)

The model was next run using the simulated values for the enthalpy and entropy, 25 kJ mol$^{-1}$ and 53 J mol$^{-1}$ K$^{-1}$. The model was unable to converge on values for the activation energy and pre-exponential factors for rates 1 and 3 that gave good representation of the data.

A comparison of Nb and SiAl on a per gram basis in FIG. 18 reveals that although the two catalysts are similar in their production of $CO_2$ with temperature, Nb is much more active in the ring opening of GVL on a per mass basis. See also Table 5. The measured acid site density of SiAl is 578 μmol g$^{-1}$ while the B.E.T. surface area is 498 m$^2$ g$^{-1}$. For Nb, the values are 135 μmol g$^{-1}$ and 118 m$^2$ g$^{-1}$. Therefore on a per acid site basis, Nb is much more active for the ring opening under the conditions of this study.

Example 8

Dehydration/Oligomerization of 5-Nonanol to Nonene 5-nonanol was dehydrated to produce an isomeric mixture of 1-, 2-, 3-, and 4-nonene over an H-ZSM-5 catalyst in a packed bed reactor operated in an upflow configuration (see FIG. 9). The catalyst (4.0 g) was loaded in a ¼" stainless steel tubular reactor with the remaining volume filled by fused silica granules that had been ground to a uniform particle size. The catalyst bed was held in place by plugs of quartz wool at the reactor entrance and exit. The tubular reactor was mounted inside of an aluminum cylinder at the center of a well insulated furnace. A Type K thermocouple was affixed to the external wall of the reactor and the temperature was controlled by a 1600 Series feedback temperature controller (Dwyer Instruments). Prior to use, the ZSM-5 catalyst was activated by thermal calcinations as previously described and the temperature was ramped to 453-473 K for the dehydration reaction. The reactor was pressurized with $H_2$ (50 cm$^3$ (STP) min$^{-1}$) to 35 bar and maintained using a back pressure regulator (GO Regulator, Model-BP-60). The 5-nonanol feed was introduced via an HPLC pump (Lab Alliance, Series 1) at a WHSV of 0.6 h$^{-1}$. The reactor effluent was collected in a gas-liquid separator (Jerguson Gage & Valve Co., Stafford, Tex., USA) at room temperature and drained for GC analysis. The reaction results are summarized in Table 6. Nearly complete conversion of the nonanol feed with >95% selectivity to nonene isomers was observed for a reaction temperature of 463 K. Side products observed included $C_{18}$ dimers from nonene and cracking products. At higher temperatures (473 K), an increased selectivity to the oligomerization and cracking products was observed at complete conversion of the 5-nonanol.

TABLE 6

Reaction results for the dehydration/oligomerization of 5-nonanol to nonene.

| Entry | Temperature (K) | Pressure (bar) | WHSV (h$^{-1}$) | Conversion (%) | Product Carbon Distribution (%) | | | |
|---|---|---|---|---|---|---|---|---|
| | | | | | nonene | $C_{18}$ olefins | $C_{27}$ olefins | other |
| 1 | 473 | 35 | 0.6 | >99 | 70 | 19 | 3 | 8 |
| 2 | 463 | 35 | 0.6 | >99 | 97 | 1 | 0 | 2 |

Example 9

Oligomerization of Nonene to $C_{18}$-Alkanes

The conversion of nonene to $C_{18}$ alkanes was performed over an Amberlyst-70 catalyst in a packed bed reactor operating in a downflow configuration. The catalyst (4.0 g, dried) was loaded into a ¼" tubular stainless steel reactor. The catalyst bed was held in place by plugs of quartz wool at the reactor entrance and exit. The tubular reactor was mounted inside of an aluminum cylinder at the center of a well insulated furnace. A Type K thermocouple was affixed to the external wall of the reactor and the temperature was controlled by a 1600 Series feedback temperature controller (Dwyer Instruments). The reactor was pressurized with He and maintained using a back pressure regulator (Tescom, Model 26-2322-26-043, Elk River, Minn., USA). The reactor temperature was ramped to 423 K for the reaction. Liquid nonene, produced from nonanol dehydration over H-ZSM-5, was introduced into the reactor using an HPLC pump (Lab Alliance Series 1). The reactor effluent was collected in a gas-liquid separator (Jerguson) at room temperature and drained for GC analysis. The reaction results are summarized in Table 7. Nonene conversions ranging from 30-80% with product selectivity predominately to dimers (~75%) and trimers (~15%) were observed for the reaction pressures and space velocities tested.

TABLE 7

Reaction results for the oligomerization of nonene to $C_{18}$-alkanes over Amberlyst-70 at 423 K.

| Entry | Pressure (bar) | WHSV (h$^{-1}$) | Conversion (%) | Product Carbon Distribution (%) | | | | |
|---|---|---|---|---|---|---|---|---|
| | | | | $C_9$ | $C_{18}$ | $C_{18}+$ | $C_{10}$-$C_{17}$ | other |
| 1 | 18 | 0.55 | 62 | 34 | 46 | 10 | 5 | 5 |
| 2 | 2 | 0.55 | 29 | 64 | 22 | 3 | 4 | 7 |
| 3 | 1 | 0.11 | 72 | 24 | 52 | 13 | 6 | 5 |

Example 10

Dehydration/Isomerization of 5-Nonanol to Linear and Branched Alkenes

Figure 20:
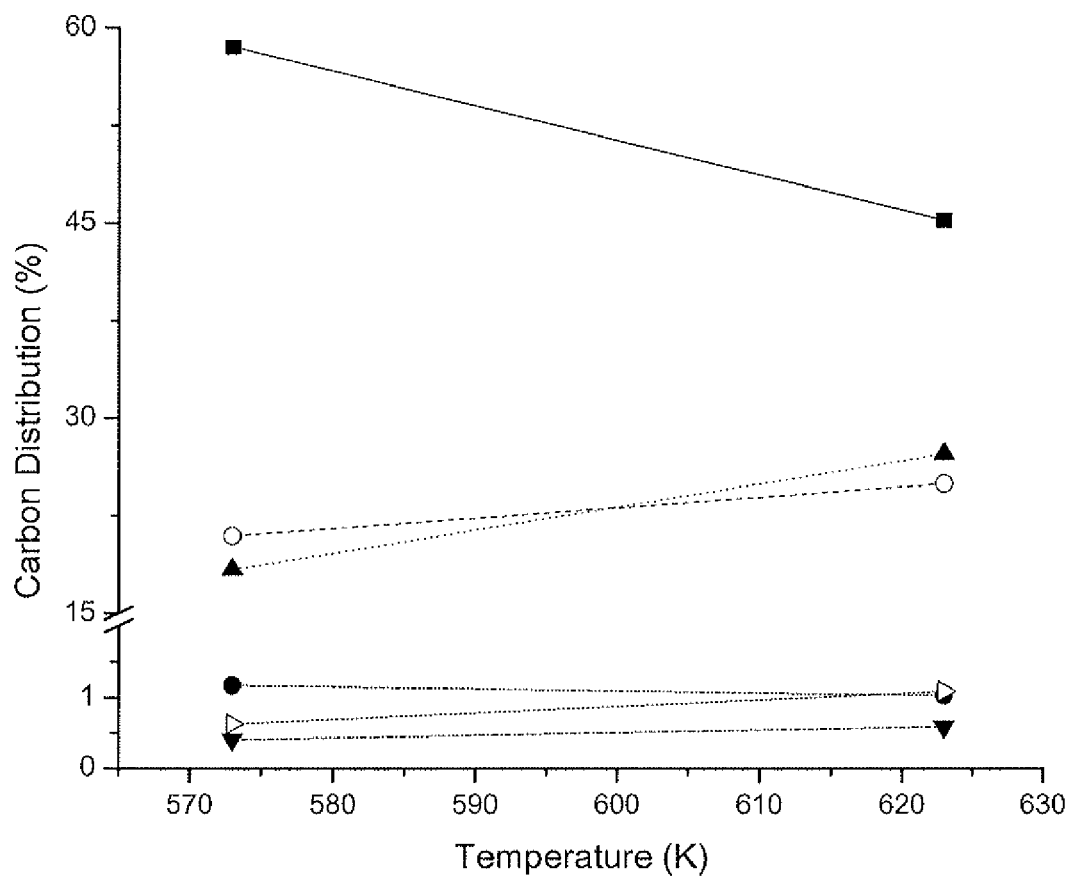
FIG. 20 is a graph depicting the dehydration and isomerization of 5-nonanol to n-nonene (■), C$_1$-octene[a] (○), C$_2$-heptene[a] (▲), C$_3$-hexene[a] (▼), cracking products[b] (●) and aromatics[c] (▷) where a. C$_1$-C$_3$ refers to hydrocarbon branches: C$_1$=methyl, C$_2$=ethyl, dimethyl, C$_3$=propyl, ethyl/methyl, trimethyl; b. refers to alkenes with less than 9 carbon atoms; c. refers to trimethyl benzene, ethyl/methyl benzene.

The dehydration and isomerization of 5-nonanol was performed over a USY-zeolite catalyst (Engelhard/BASF, BASF AG, Ludwigshafen, Germany). The catalyst was loaded into a ¼" tubular stainless steel reactor operating in an upflow configuration. Prior to reaction, the catalyst was calcined in situ under flowing air (25 cm$^3$ (STP) min$^{-1}$) by ramping the temperature (1 h) to 773 K and holding for 2 h. The reactor was cooled to the reaction temperature and pure 5-nonanol (Sigma Aldrich) was introduced using an HPLC pump (Lab Alliance Series 1). The reactor effluent was collected at room temperature in a gas-liquid separator (Jerguson) and drained for GC analysis. Results for the 5-nonanol dehydration and isomerization at atmospheric pressure and a WHSV of 0.6 hr$^{-1}$ at two temperatures (573 and 623 K) are shown in FIG. 20.

Example 11

Decarboxylation of γ-Valerolactone to Butene

GVL was converted to butene and $CO_2$ over an amorphous silica alumina catalyst. The catalyst was loaded into in a ¼" tubular stainless steel reactor operating in an upflow configuration. The catalyst bed was held in place by plugs of quartz wool at the reactor entrance and exit. The tubular reactor was mounted inside of an aluminum cylinder at the center of a well insulated furnace (Applied Test Systems). A Type K thermocouple (Omega) was affixed to the external wall of the reactor and the temperature was controlled by a 1600 Series feedback temperature controller (Dwyer Instruments). A GVL solution was introduced into the reactor using an HPLC pump (Lab Alliance Series 1). The reactor effluent was collected at room temperature in a gas-liquid separator (Jerguson) and drained for GC analysis. The reactor pressure was maintained at atmospheric pressure for all experiments.

A 30 wt % GVL feed was reacted with and without the addition of $H_2SO_4$ (0.04 M) to the feed solution. The results for the 30 wt % GVL feed solutions are shown in Table 4, above. The conversion data in Table 4 were calculated from the unreacted GVL observed in the liquid effluent. High butene yields were observed for GVL feeds (10-30 wt %) with and without $H_2SO_4$. The yield to mixed butene isomers was calculated from the observed gas phase effluents. No deactivation was observed over the total reaction time (40 h).

REFERENCES

J. Chheda, G. Huber, J. A. Dumesic, Angew. Chem. Int. Ed. (2007) 46(38), 7164-7183.
R. D. Cortright, R. R. Davda, J. A. Dumesic, Nature (2002) 418(6901) 964-967.

B. Girisuta, L. P. B. M. Janssen, H. J. Heeres, Ind. Eng. Chem. Res. (2007) 46(6) 1696-1708.

S. Koppatz, C. Pfeifer, R. Rauch, H. Hofbauer, T. Marquard-Hoellenstedt, M. Specht, Fuel Proc. Tech. (2009) In Press.

E. L. Kunkes, D. A. Simonetti, R. M. West, J. C. Serrano-Ruiz, C. A. Gaertner, J. A. Dumesic, Science (2008) 322 (5900) 417-421.

J. Robinson, et. al. Biomass Bioenergy (2004) 26(5), 473-483.

S. Zhu, et. al., Green Chem. 8, 325-327 (2006).

G. W. Huber, A. Corma, Angew. Chem. Int. Ed. (2007), 46, 7184-7201.

C. H. Christensen, J. Rass-Hansen, C. C. Marsden, E. Taarning and K. Egeblad, Chem Sus Chem, (2008) 1, 283-289.

C. Gaertner, J. C. Serrano-Ruiz, D. J. Braden and J. A. Dumesic, Journal of Catalysis, (2009) accepted.

M. Renz, Eur J Org Chem (2005) 979-988.

R. M. West, Z. Y. Liu, M. Peter, and J. A. Dumesic, Chem Sus Chem (2008) 1, 417-424.

J. Abbot and B. W. Wojciechowski, J. Catal., (1987) 108, 346-355.

Arno de Klerk, Ind. Eng. Chem. Res. (2005) 44, 3887-3893.

J. A. Miller, J. A. Nelson and M. P. Byrne, J. Org. Chem. (1993) 58, 18-20.

S. W. Fitzpatrick. Manufacture of furfural and levulinic acid by acid degradation of lignocellulose. WIPO Published Application 89/10362 to Biofine Incorporated, (1990).

P. Kumar, D. M. Barrett, M. J. Delwiche and P. Stroeve, Ind. Eng. Chem. Res. (2009), 48, 3713-3729.

A. S. Mamman, J. M. Lee, Y. C. Kim, I. T. Hwang, N. J. Park, Y. K. Hwang, J. S. Chang, J. S. Hwang, Biofuels Bioproducts & Biorefining (2008), 2(5), 438-454.

J. C. Serrano-Ruiz, J. Luettich, A. Sepulveda-Escribano, F. J. Rodriguez-Reinoso, J. Catal. 241 45 (2006).

What is claimed is:

1. A method for converting glucose to n-butenes the method comprising:
    (a) hydrolyzing glucose derived from any source in an aqueous, acid-catalyzed reaction to yield a product mixture comprising levulinic acid and formic acid; then
    (b) converting at least a portion of the formic acid present in the product mixture to $H_2$ and $CO_2$ without separating the levulinic acid and formic acid present in the product mixture; and
    (c) reducing at least a portion of the levulinic acid present in the product mixture to γ-valerolactone using the $H_2$ produced in step (b); and then
    (d) decarboxylating at least a portion of the γ-valerolactone from step (c) by contacting it with a solid acid catalyst, to yield a product mixture comprising n-butenes.

2. The method of claim 1, wherein step (d) comprises decarboxylating the γ-valerolactone by reacting it with a mineral acid selected from the group consisting of sulfuric acid, hydrochloric acid, nitric acid, phosphoric acid, boric acid, hydrofluoric acid, hydrobromic acid, acetic acid, acetic anhydride, oxalic acid, and combinations thereof.

3. The method of claim 1, wherein step (d) comprises decarboxylating the γ-valerolactone by reacting it with a heterogeneous catalyst comprising a metal selected from the group consisting of Fe, Co, Ni, Ru, Rh, Pd, Os, Ir, Pt, Ag, Au, Ru and combinations thereof.

4. The method of claim 1, wherein step (a) comprises hydrolyzing the glucose by reacting it with an acid.

5. The method of claim 4, wherein step (a) comprises hydrolyzing the glucose by reacting it with a mineral acid selected from the group consisting of sulfuric acid, hydrochloric acid, nitric acid, phosphoric acid, boric acid, hydrofluoric acid, hydrobromic acid, oxalic acid, acetic acid, acetic anhydride, and combinations thereof.

6. The method of claim 1, wherein step (b) comprises converting the converting the formic acid present in the product mixture to $H_2$ and $CO_2$ by contacting the product mixture with a heterogeneous catalyst comprising a metal selected from the group consisting of Fe, Co, Ni, Ru, Rh, Pd, Os, Ir, Pt, Ag, Au, and combinations thereof.

7. The method of claim 6, wherein step (b) comprises contacting the product mixture with a heterogeneous catalyst comprising Ru.

8. The method of claim 1, wherein step (c) further comprises extracting the γ-valerolactone so formed into a solvent comprising a polar, aprotic solvent.

9. The method of claim 1, wherein step (c) further comprises evaporating the γ-valerolactone so formed.

* * * * *